(12) United States Patent
Hashmi et al.

(10) Patent No.: US 7,344,841 B2
(45) Date of Patent: Mar. 18, 2008

(54) REAL-TIME MONITORING OF NUCLEIC ACID TARGET-IDENTIFYING SIGNALS

(75) Inventors: Ghazala Hashmi, Holmdel, NJ (US); Michael Seul, Fanwood, NJ (US); Joachim Messing, Somerset, NJ (US)

(73) Assignee: BioArray Solutions Ltd., Warren, NJ (US)

( * ) Notice: Subject to any disclaimer, the term of this patent is extended or adjusted under 35 U.S.C. 154(b) by 51 days.

(21) Appl. No.: 11/438,161

(22) Filed: May 22, 2006

(65) Prior Publication Data

US 2007/0048762 A1    Mar. 1, 2007

Related U.S. Application Data

(62) Division of application No. 10/238,439, filed on Sep. 9, 2002, now Pat. No. 7,157,228.

(51) Int. Cl.
*C12Q 1/68* (2006.01)
*C07H 21/02* (2006.01)
*C07H 21/04* (2006.01)

(52) U.S. Cl. ............... 435/6; 536/23.1; 536/24.3
(58) Field of Classification Search ............ 435/6, 435/91.2; 536/23.1, 24.3
See application file for complete search history.

(56) References Cited

U.S. PATENT DOCUMENTS

| | | | |
|---|---|---|---|
| 5,075,217 A | 12/1991 | Weber | |
| 5,364,759 A | 11/1994 | Caskey et al. | |
| 5,604,097 A | 2/1997 | Brenner | |
| 5,639,606 A | 6/1997 | Willey | |
| 5,643,765 A | 7/1997 | Willey | |
| 5,650,489 A | 7/1997 | Lam et al. | |
| 5,837,501 A | 11/1998 | Beumer et al. | |
| 5,900,097 A | 5/1999 | Lough et al. | |
| 6,060,243 A | 5/2000 | Tang et al. | |
| 6,150,095 A | 11/2000 | Southern et al. | |
| 6,153,389 A | 11/2000 | Haarer et al. | |
| 6,156,502 A | 12/2000 | Beattie | |
| 6,203,993 B1 | 3/2001 | Shuber et al. | |
| 6,221,598 B1 | 4/2001 | Schumm et al. | |
| 6,238,863 B1 | 5/2001 | Schumm et al. | |
| 6,251,592 B1 | 6/2001 | Tang et al. | |
| 6,306,643 B1 | 10/2001 | Gentalen et al. | |
| 6,355,431 B1 | 3/2002 | Chee et al. | |
| 6,368,799 B1 | 4/2002 | Chee | |
| 6,399,328 B1 | 6/2002 | Vournakis et al. | |
| 6,521,747 B2 | 2/2003 | Anastasio et al. | |

FOREIGN PATENT DOCUMENTS

| | | | |
|---|---|---|---|
| WO | WO99/36564 | | 7/1999 |
| WO | WO01/25002 A1 | | 4/2001 |
| WO | WO02/079490 A2 | | 10/2002 |

OTHER PUBLICATIONS

R. Lynn Alford, C. Thomas Caskey, "DNA analysis in forensics, disease and animal/plant identification," *Current Opinion in Biotechnology*, vol. 5: 29-33 (1994).
D.H. Oliver, et al., "Use of Single Nucleotide Polymorphisms (SNP) and Real-Time Polymerase Chain Reaction for Bone Marrow Engraftment Analysis," *Journal of Molecular Diagnostics*, vol. 2, No. 4: 202-208 (2000).
S. Easteal, "DNA fingerprinting by PCR amplification of HLA genes," *DNA and Criminal Justice*, 121-127 (Human Genetics Group, John Curtin School of Medical Research, 1991).
E. Moller, S. Sumitran-Karuppan, "The use of magnetic beads coated with soluble HLA class I or class II proteins in antibody screening and for specificity determination of donor-reactive antibodies," *Transplantation*, vol. 61, No. 10: 1539-1545 (Williams & Wilkins, 1996).
Wang, et al., "Large-scale identification, mapping, and genotyping of single-nucleotide polymorphisms in the human genome," *Science*, vol. 280, No. 5366: 1077-1082 (1998).
A.C. Syvanen, et al., "Identification of individuals by analysis of biallelic DNA markers using PCR and solid-phase minisequencing," *American Journal of Human Genetics*, vol. 52: 46-59 (1993).
Philippe Latour, et al., "Polymorphic short tandem repeats for diagnosis of the Charot-Marie-Tooth IA duplication," *Clinical Chemistry*, vol. 47, No. 5: 829-837 (2001).
E.S. Lander, "The new genomics: global views of biology," *Science*, vol. 274, No. 5287: 536-539 (1996).
Sacchetti, et al., "Efficiency of two dfferent nine-loci short tandem repeat systems for DNA typing purposes," *Clinical Chemistry*, vol. 25, No. 2: 178-183 (1999).

(Continued)

*Primary Examiner*—Ethan Whisenant
(74) *Attorney, Agent, or Firm*—Eric P. Mirabel

(57) ABSTRACT

This invention provides compositions and methods for genetic testing of an organism and for correlating the results of the genetic testing with a unique marker that unambiguously identifies the organism. The markers may be internal markers, such as for example single nucleotide polymorphisms (SNPs), short tandem repeats (STRs), or other sites within a genomic locus. Alternatively, the markers may be external, such that they are separately added to the genetic sample before testing.

9 Claims, 18 Drawing Sheets

OTHER PUBLICATIONS

Garber, "Genome research: more SNPs on the way," *Science*, vol. 281, No. 5384: 1788 (1998).

P.J. Bickel, "Discussion of the evaluation of forensic DNA evidence,'" *Proceedings of the National Academy of Science of the United States of America*, vol. 92: 5497 (1997).

PROMEGA Product Technical Manual, "GenePrint(R) Fluorescent STR Systems," Technical Manual No. D006 (1999).

Cheng, et al., "A synthetic peptide derived from p34cdc2 is a specific and efficient substrate of src-family tyrosine kinases," *J. Biol. Chem.*, vol. 267, No. 13: 9248-9256 (1992).

"Genes Linked to Alzheimer's Disease," Genetics of Alzheimers Disease, http://www.neurosci.pharm.utoledo.edu/AD/genetics.htm.

Heinrich, et al., "Interleukin-6-type cytokine signaling through the gp130/Jak/STAT pathway," *Biochem. J.*, vol. 334: 297-314 (1998).

Kolch, "Meaningful relationships: the regulation of the Ras/Raf/MEK/ERK pathway by protein interactions," *Biochem. J.*, vol. 351: 289-305 (2000).

ASCO Online, "Value of New Agents and New Targets Assessed," http://www.asco.org/prof/and/2002/mon/value.htm (2002).

Vilain, "CYPs, SNPs, and molecular diagnosis in the postgenomic era," *Clinical Chemistry*, vol. 44: 2403-2404 (1998).

Baldwin, et al., "Phosphorylation of gastrin-17 by epidermal growth factor-simulated tyrosine kinase," *Nature*, vol. 301, No. 5899: 435-437 (1983).

Casnellie, et al., "Phosphorylation of synthetic peptides by a tyrosine protein kinase from the particulate fraction of a lymphoma cell line," *Proc. Nat'l Acad. Sci.* USA, vol. 79: 282:286 (1982).

Shon, "Application note: new best practices for biosample management: moving beyond freezers," *American Biotechnology Laboratory*, vol. 23, No. 2: 10-13 (2005).

Finkel, et al., "Barcoding the microworld," *Analytical Chemistry*, 353-359 (Oct. 1, 2004).

EXON 7 POLYMORPHISMS

```
  1   tttacaagta ctacaagcaa aacactggta ctttcattgt tatcttttca tataaggtaa
 61   ctgaggccca gagagattaa ataacatgcc caaggtcaca caggtcatat gatgtggagc
121   caggttaaaa atataggcag aaagactcta gagaccatgc tcagatcttc cattccaaga
181   tccctgatat ttgaaaaata aaataacatc ctgaatttta ttgttattgt tttttataga
241   acagaactga aactgactcg gaaggcagcc tatgtgagat acttcaatag ctcagCcttc
301   ttCttcttaG GgttCTttgT ggtgtttTtA tctgTgcttc cctatgcacT aatcaaAGga
361   atcatcctcC GgaaaATatt caCcaccAtc TCattctgCa ttgttcTgCG catggcggtc
421   actCGgCaAt ttccctGGgc tgtaCAaaCa TgGtatgaCT ctcTtggagc aataaacaaa
481   atacaggtaa tgtaccataa tgctgcatta tatactatga tttaaataat cagtcaatag
541   atcagttcta atgaactttg caaaaatgtg cgaaaagata gaaaaagaaa tttccttcac
601   taggaagtta taaagttgc cagctaatac taggaatgtt caccttaaac ttttcctagc
661   atttctctgg acagtatgat ggatgagagt ggcatttatg caaattacct taaaatccca
721   ataatactga tgtagctagc agctttgaga aa
```

FIG. 4 (SEQ ID NO. 1)

```
  1   cactgtagct gtactaccttccatctcctc aacctattcc aactatctga atcatgtgcc
 61   cttctctgtg aacctctatc ataatacttg tcacactgta ttgtaattgt ctcttttact
121   ttcccttgta tcttttgtgc atagcagagt acctgaaaca ggaagtattt taaatatttt
181   gaatcaaatg agttaataga atctttacaa ataagaatat acacttctgc ttaggatgat
241   aattggaggc aagtgaatcc tgagcgtgat ttgataatga cctaataatg atgggtttta
301   tttccagact tcaCttctaa tgAtgattat gggagaactg gagccttcag agggtaaaat
361   taagcacagt ggaagaattt cattctgttc tcagtttttcc tggattatgc ctggcaccat
421   taaagaaaat AtCAtctTtg gtgtttccta tgatgaatat agatacagaa gcgtcatcaa
481   agcatgccaa ctagaAgagG taagaaacta tgtgaaaact ttttgattat gcatatgaac
541   ccttcacact acccaaatta tatatttggc tccatattca atcggttagt ctacatatat
601   ttatgtttcc tctatgggta agctactgtg aatggatcaa ttaataaaac acatgaccta
661   tgctttaaga agcttgcaaa cacatgaaat aaatgcaatt tatttttta ataatgggtt
721   catttgatca caataaatgc.attttatgaa atggtgagaa ttttgttcac tcattagtga
781   gacaaacgtc tcattggtta tttatatggc atgcatatag tgatatgtgg t
```

FIG. 5A (SEQ ID NO. 2)

Probe design for SNP identification within Exon 10 of CFTR gene WILD-TYPE dbSNP 1800092
gaaaat AtCAtctTtg g (SEQ ID NO. 3)
gaaaat AtGAtctTtg g (SEQ ID NO. 4)
gaaaat AtCGtctTtg g (SEQ ID NO. 5)
gaaaat AtGGtctTtg g (SEQ ID NO. 6)

dbSNP 1800093
gaaaat AtCAtctGtg g (SEQ ID NO. 7)
gaaaat AtGAtctGtg g (SEQ ID NO. 8)
gaaaat AtCGtctGtg g (SEQ ID NO. 9)
gaaaat AtGGtctGtg g (SEQ ID NO. 10)

dbSNP1801178
gaaaat GtCAtctTtg g (SEQ ID NO. 11)
gaaaat GtGAtctTtg g (SEQ ID NO. 12)
gaaaat GtCGtctTtg g (SEQ ID NO. 13)
gaaaat GtGGtctTtg g (SEQ ID NO. 14)

gaaaat GtCAtctGtg g (SEQ ID NO. 15)
gaaaat GtGAtctGtg g (SEQ ID NO. 16)
gaaaat GtCGtctGtg g (SEQ ID NO. 17)
gaaaat GtGGtctGtg g (SEQ ID NO. 18)

DeltaF508
gaaaat AtCAttg gtgt (SEQ ID NO. 19)
gaaaat AtGAttg gtgt (SEQ ID NO. 20)
gaaaat AtCGttg gtgt (SEQ ID NO. 21)
gaaaat AtGGttg gtgt (SEQ ID NO. 22)
gaaaat GtCAttg gtgt (SEQ ID NO. 23)
gaaaat GtGAttg gtgt (SEQ ID NO. 24)
gaaaat GtCGttg gtgt (SEQ ID NO. 25)
gaaaat GtGGttg gtgt (SEQ ID NO. 26)

I507
gaaaat AtCtttg gtgt (SEQ ID NO. 27)
gaaaat AtGtttg gtgt (SEQ ID NO. 28)
gaaaat GtCtttg gtgt (SEQ ID NO. 29)
gaaaat GtGtttg gtgt (SEQ ID NO. 30)

Other Polymorphisms dbSNP213950
tcaCttctaa tgAtgattat (SEQ ID NO. 31)
tcaCttctaa tgGtgattat (SEQ ID NO. 32)

dbSNP1800089
tcaTttctaa tgAtgattat (SEQ ID NO. 33)
tcaTttctaa tgGtgattat (SEQ ID NO. 34)

dbSNP1800094
ctagaAgagG taagaaa (SEQ ID NO. 35)
ctagaGgagG taagaaa (SEQ ID NO. 36)

dbSNP1800095
ctagaAgagG taagaaa (SEQ ID NO. 37)
ctagaAgagA taagaaa (SEQ ID NO. 38)

FIG. 5B

SEQUENCE LISTING

<160> NUMBER OF SEQ ID NOS: 39

<210> SEQ ID NO 1
<211> LENGTH: 752
<212> TYPE: DNA
<213> ORGANISM: Homo sapiens

<400> SEQUENCE: 1

```
tttacaagta ctacaagcaa aacactggta ctttcattgt tatcttttca tataaggtaa      60
ctgaggccca gagagattaa ataacatgcc caaggtcaca caggtcatat gatgtggagc     120
caggttaaaa atataggcag aaagactcta gagaccatgc tcagatcttc cattccaaga     180
tccctgatat ttgaaaaata aaataacatc ctgaatttta ttgttattgt tttttataga     240
acagaactga aactgactcg gaaggcagcc tatgtgagat acttcaatag ctcagccttc     300
ttcttctcag ggttctttgt ggtgttttta tctgtgcttc cctatgcact aatcaaagga     360
atcatcctcc ggaaaatatt caccaccatc tcattctgca ttgttctgcg catggcggtc     420
actcggcaat ttccctgggc tgtacaaaca tggtatgact ctcttggagc aataaacaaa     480
atacaggtaa tgtaccataa tgctgcatta tatactatga tttaaataat cagtcaatag     540
```

```
atcagttcta atgaactttg caaaaatgtg cgaaaagata gaaaagaaa tttccttcac      600 taggaagtta taaagttgc cagctaatac taggaatgtt caccttaaac ttttcctagc      660
atttctctgg acagtatgat ggatgagagt ggcatttatg caaattaccct taaaatccca    720 ataatactga tgtagctagc agctttgaga aa                                   752
```

<210> SEQ ID NO 2
<211> LENGTH: 831
<212> TYPE: DNA
<213> ORGANISM: Homo sapiens

<400> SEQUENCE: 2

```
cactgtagct gtactacctt ccatctcctc aacctattcc aactatctga atcatgtgcc      60
cttctctgtg aacctctatc ataatacttg tcacactgta ttgtaattgt ctctttact     120 ttcccttgta tcttttgtgc atagcagagt acctgaaaca ggaagtattt taaatatttt    180
gaatcaaatg agttaataga atctttacaa ataagaatat acacttctgc ttaggatgat    240
aattggaggc aagtgaatcc tgagcgtgat ttgataatga cctaataatg atgggtttta    300
tttccagact tcacttctaa tgatgattat gggagaactg gagccttcag agggtaaaat    360
taagcacagt ggaagaattt cattctgttc tcagttttcc tggattatgc ctggcaccat    420
taaagaaaat atcatctttg gtgtttccta tgatgaaata agatacagaa gcgtcatcaa    480
agcatgccaa ctagaagagg taagaaacta tgtgaaaact ttttgattat gcatatgaac    540
ccttcacact acccaaatta tatatttggc tccatattca atcggttagt ctacatatat    600
ttatgtttcc tctatgggta agctactgtg aatggatcaa ttaataaaac acatgaccta    660
tgctttaaga agcttgcaaa cacatgaaat aaatgcaatt tatttttttaa ataatgggtt    720 catttgatca caataaatgc attttatgaa atggtgagaa ttttgttcac tcattagtga    780
gacaaacgtc tcaatggtta tttatatggc atgcatatag tgatatgtgg t             831
```

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3

```
gaaaatatca tctttgg                                                    17
```

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4

```
gaaaatatga tctttgg                                                    17
```

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      probe -continued

```
<400> SEQUENCE: 5
gaaaatatcg tctttgg                                                17

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
gaaaatatgg tctttgg                                                17

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
gaaaatatca tctgtgg                                                17

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
gaaaatatga tctgtgg                                                17

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
gaaaatatcg tctgtgg                                                17

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
gaaaatatgg tctgtgg                                                17

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
```

-continued

```
gaaaatgtca tctttgg                                            17

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
gaaaatgtga tctttgg                                            17

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
gaaaatgtcg tctttgg                                            17

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
gaaaatgtgg tctttgg                                            17

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
gaaaatgtca tctgtgg                                            17

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
gaaaatgtga tctgtgg                                            17

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
```
gaaaatgtcg tctgtgg                                                    17

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
gaaaatgtgg tctgtgg                                                    17

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
gaaaatatca ttggtgt                                                    17

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
gaaaatatga ttggtgt                                                    17

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
gaaaatatcg ttggtgt                                                    17

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
gaaaatatgg ttggtgt                                                    17

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
gaaaatgtca ttggtgt                                                    17

```
<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
gaaaatgtga ttggtgt                                                   17

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
gaaaatgtcg ttggtgt                                                   17

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
gaaaatgtgg ttggtgt                                                   17

<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
gaaaatatct ttggtgt                                                   17

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
gaaaatatgt ttggtgt                                                   17

<210> SEQ ID NO 29
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
gaaaatgtct ttggtgt                                                   17
```

```
<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
gaaaatgtgt ttggtgt                                                   17

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
tcacttctaa tgatgattat                                                20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
tcacttctaa tggtgattat                                                20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
tcatttctaa tgatgattat                                                20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
tcatttctaa tggtgattat                                                20

<210> SEQ ID NO 35
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
ctagaagagg taagaaa                                                   17
```

-continued

```
<210> SEQ ID NO 36
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
ctagaggagg taagaaa                                                  17

<210> SEQ ID NO 37
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
ctagaagagg taagaaa                                                  17

<210> SEQ ID NO 38
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
ctagaagaga taagaaa                                                  17

<210> SEQ ID NO 39
<211> LENGTH: 11
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
cttatttccc t                                                        11
```

REAL-TIME MONITORING OF NUCLEIC ACID TARGET-IDENTIFYING SIGNALS

RELATED APPLICATIONS

This application is a divisional of U.S. application Ser. No. 10/238,439, filed Sep. 9, 2002, now U.S. Pat. No. 7,157,228 priority to which is hereby claimed.

BACKGROUND OF THE INVENTION

Genetic analysis is widely used in basic and applied research as well as in diagnostics to screen, to profile and to genotype patients. Clinical laboratories currently offer genetic tests for more than 300 diseases or conditions including the analysis of mutations in the BRCA1 and BRCA2 genes, as well as in the p53, N—, C— and K—RAS, cytochrome P450, CFTR, HLA class I and II, Duchenne Muscular Dystrophy and beta-globin genes. The test menu continues to grow as advances in the Human Genome Project lead to the identification of genetic determinants that play a role in causing disease.

Genetic testing involves the analysis of genes and/or chromosomes to detect inheritable or other mutations as well as chromosome aberrations in order to provide a diagnosis for disease susceptibility. In addition, protein levels are monitored to obtain an indication of disease progression or response to treatment. Genetic testing has been used to diagnose and to monitor cancer, as well as to assess the pre-symptomatic risk of individuals to develop the disease. At present, for example, members of families diagnosed for several diseases such as Atexia-telangiectasia, Bloom's syndrome, Fanconi's anemia or Xeroderma Pigmentosum can be tested for the occurrence of mutations in the respective genes. In addition, several mutations in the regulatory gene p53 also have been correlated with the risk of developing different types of cancers. Those who inherit p53 mutations are at high risk of developing sarcoma, brain tumors or leukemia.

The standards analysis methods used in genetic analysis, DNA typing and DNA fingerprinting include (1) analysis of variable Number of Tandem Repeats (VNTR) (e.g., Nakamura et al., Science, Vol. 235, pp. 1616-1622 (1987), (2) analysis of Short Tandem Repeats (STR) (e.g., Edwards et al., Am. J. Hum. genet. Vol. 49, pp. 746-756 (1991); Ricciardone et al., Biotechniques, Vol. 23, pp. 742-747 (1997), (3) analysis of Single Nucleotide Polymorphisms (SNP) (e.g., Nickerson et al., Proc. Natl. Acad. Sci. U.S.A., Vol. 87, pp. 8923-8927 (1990); Nikiforov et al. Nucleic Acids Res. Vol. 22, pp. 4167-4175 (1994); Ross et al., Anal. Chem. Vol. 69, pp. 4197-4202)), (d) analysis of Restriction Fragment Length Polymorphisms (RFLPs) (e.g., Botstein et al. Am. J. Hum. Genet. Vol. 32, pp. 314-331 (1980)), and (4) analysis of mitochondrial DNA sequences. VNTR and STR analyses utilize simple or multiplex Polymerase Chain Reaction (PCR) technology (e.g., Mullis et al., Cold Spring Harbor Symp. Quant. Biol., Vol. 51, pp. 263-273 (1986); Mullis et al., Science, Vol. 239, Vol. 487-491 (1988)). RFLP analysis utilizes restriction enzyme digestion of DNA followed by DNA hybridization techniques with labeled probes; and mitochondrial DNA sequence analysis utilizes a combination of PCR technology and conventional dideoxy sequencing in a process known as cycle sequencing.

Variations among individuals in the number of STRs in specific genetic locations have been shown to be associated with several common genetic diseases. For example, unstable doublet repeats are known to be associated with disease states such as cystic fibrosis and colorectal cancer. Certain unstable triplet repeats are known to be associated with several genetic diseases, including Kennedy's disease, fragile-X syndrome and Myotonic dystrophy. Huntington's disease in particular has been investigated extensively and STRs have been mapped across a section of the gene to identify 51 triplet repeats spanning a 1.86 Mbp DNA segment. Higher-order repeats, such as tetramers, have also been associated with particular disease states including Huntington's disease and spinocerebellar ataxia type 1.

DNA typing based on the standard laboratory methods requires extensive sample preparation and significant post-PCR processing. The latter includes the steps of restriction enzyme digestion, agarose/acrylamide gel electrophoresis, sequence analysis or a combination of these methods. These multi-step protocols introduce considerable bias in the data and are labor intensive and time consuming.

DNA fingerprinting, also referred to as identity testing, relies on the analysis of highly polymorphic genetic loci to provide unambiguous molecular identification of individuals. A variety of polymorphic markers are available for this purpose including restriction fragment length polymorphisms (RFLPs), single nucleotide polymorphisms (SNPs), STRs/microsatellites and variable number of tandem repeats (VNTRs)/minisatellites. RFLP analysis requires enzyme digestion of genomic DNA followed by gel electrophoresis and hybridization of radiolabeled probes to the gel. The complexity of this procedure has prevented RFLP analysis from being widely adopted for identity testing. SNPs, wherein one allele differs from another allele at a single position, occur with an average frequency of 1 in 1,000 bases in both coding and non-coding regions and constitute 90% of all polymorphisms within the human genome (Brooker, Gene, 234:177-186 (1999)). They have been used for the mapping of genes associated with diseases such as cancer, for the typing of donors for bone marrow engraftment, and for studying inheritance within the context of population genetics. (Kwok at al., Mol. Med. Today, 538-543, (1999)) However, while suitable sets of SNPs are being developed to provide unambiguous DNA fingerprints, those new markers will require careful validation. In addition, in comparison to the STR markers commonly used at present, the set of SNP markers required to ensure a given probability of exclusion of ambiguity will be large. Both SNPs and STR polymorphisms can be used as markers, however about 7 to 12 SNPs per STR polymorphism are required to get a power of exclusion of 99.73%.

STRs and VNTRs are highly informative polymorphic markers. Many genetic loci contain a polymorphic STR region consisting of short, repetitive sequence elements, typically 3 to 7 bases in length. Trimeric and tetrameric STRs occur as frequently as once per 15,000 bases of a given sequence and are widely used for identity typing in parentage and forensic analysis. In contrast to the case for SNPs, where a large number of loci are needed for exclusion, only nine specific STR loci are required to provide a combined average power of exclusion of 99.73%. (Alford et. al Current Opinion in Biotechnology, 29-33 (1994), Latour et al, 829-37 (2001). STRs may be amplified via the polymerase chain reaction (PCR) by employing specific primer sequences directed to the regions flanking the tandem repeat.

Other polymorphisms arising from differences in the number of repeated elements in an allele include variable number of tandem repeats (VNTRs)/minisatellites, which are tandem repeats of a short sequence containing from 9 to 60 bases, and microsatellites which contain from one to five bases. Minisatellites and microsatellites are generally considered to be a subclass of VNTRs. Since it is estimated that about 500,000 microsatellite repeats are distributed throughout the human genome, at an average spacing of 7,000 bases, VNTR regions also can be used in identity testing.

In conventional laboratory practice, STRs and VNTRs are amplified by PCR using radio-labeled or fluorescence-labeled primers. The PCR products are separated by gel electrophoresis or capillary electrophoresis for identification.

In conventional implementations of genetic testing, information relating to sample and patient identification is recorded manually, typically involving the completion of bar coded labels which are affixed to sample collection containers. Such labeling procedures represent a potentially significant source of error involving mishandling, mislabeling and switching of samples.

Thus a need exists for a mechanism whereby collected known biological samples would be unambiguously marked and identified at the time of collection. This would safeguard against the mishandling, mislabeling and switching of samples during analysis.

SUMMARY OF THE INVENTION

This invention provides methods of analyzing STRs and related repeated sequence elements in parallel, in order to unambiguously link samples with genetic test results and patient identity. Specifically, the present invention provides methods for recording a molecular identification (ID) concurrently faith the completion of a genetic analysis, by linking a patient's genetic profile to a patient's molecular fingerprint, thereby minimizing the incidence of inadvertent mishandling of samples and permitting unambiguous authentication by comparison against previously recorded, or subsequently recorded molecular identification.

One aspect of this invention is to provide a composition for analyzing a target nucleic acid sequence obtained from a patient sample while concurrently providing the genetic fingerprint of the patient. This composition comprises a first set of probes and a second set of probes. The first set of probes comprises oligonucleotide probes that hybridize to a target nucleic acid sequence obtained from a patient sample for genetic testing, while the second set comprises oligonucleotide probes for hybridizing to a plurality of polymorphic markers. The hybridization to these markers provides a genetic fingerprint that identifies the patient. The probes of these two sets are attached to beads that are associated with a chemically or physically distinguishable characteristic that can be used to uniquely identify the probes that are attached to the beads.

Another aspect of this invention is to provide a method for analyzing a target nucleic acid sequence obtained from a patient sample while concurrently providing the genetic fingerprint of the patient. This method comprises providing a first set of probes and a second set of probes. The first set of probes comprises oligonucleotide probes that hybridize to a target nucleic acid sequence obtained from a patient sample for genetic testing, while the second set of probes comprises oligonucleotide probes for hybridizing to a plurality of polymorphic markers. The hybridization to these markers provides a genetic fingerprint that allows the identification of the patient. The probes of the first and the second set are attached to beads that are associated with a chemically or physically distinguishable characteristic that uniquely identifies the probes that are attached to said beads. This method further comprises contacting a target sequence and a plurality of polymorphic markers to the first and second set of probes, and then detecting the hybridization between the probes of the first set to the target sequence and detecting the hybridization between the probes of the second set to the polymorphic markers.

Another aspect of this invention is to provide a method of analyzing a target nucleic acid sequence obtained from a patient sample. This method involves providing a means for uniquely linking the sequence analysis with the sample and comprises providing e set of probes comprising oligonucleotide probes that hybridize to a target nucleic acid sequence obtained from a patient sample. The probes are attached to beads that are associated with a chemically or physically distinguishable characteristic that uniquely identifies the probes attached to the beads. The method further comprises contacting the oligonucleotide probes with a solution containing the target nucleic acid sequence to allow the target sequence to hybridize with the corresponding probe and detecting the hybridization of the probes with the target sequence. The solution is labeled with a molecular label that uniquely identifies the target solution, such that the patient identity is determined by interrogating the label. The label may be added to the sample before or after the solution is introduced to the oligonucleotides, or at the same time.

Another aspect of this invention is to provide a method of determining the number of tandem nucleotide repeats in a target nucleic acid sequence, where the tandem repeats are flanked at each side by a non-repeat flanking sequence. The method comprises providing a set of oligonucleotide probes attached to beads, wherein each bead is associated with a chemically or physically distinguishable characteristic that uniquely identifies the probe attached to the bead. Each probe is capable of annealing to the target sequence and contains an interrogation site. The set of probes is designed such that the probes differ in the number of repeated nucleotides. When the probes are annealed to the target sequence to form hybridization complexes, the interrogation site of each probe is aligned with a target site located either within the tandem repeats or outside the tandem repeats. The method further comprises contacting a target sequence to the oligonucleotide probes, so that the target sequence forms hybridization complexes with the probes. The hybridization complexes between the target sequence and probes in the set are interrogated in parallel to determine whether the interrogation site of the probes end outside the repeats of the target or inside the repeats of the target. The number of repeats in the target sequence is also determined.

Yet another aspect of this invention is to provide a method of sequence-specific amplification of assay signals produced in the analysis of a target nucleic acid sequence. This method permits real-time monitoring of the amplified signal and comprises providing a temperature-controlled sample containment device that permits real-time recording of optical assay signals produced within the device. The method further comprises providing a temperature control means for controlling the temperature of the device and providing, within the sample containment device, a set of interrogation oligonucleotide probes. These probes are capable of forming a hybridization complex with the target nucleic acid and are attached to beads. Each bead is associated with a chemically or physically distinguishable characteristic that identifies the probe attached to the bead. The oligonucleotide probes are contacted with the target sequence to form a hybridization complex between the probes and the target sequence. This hybridization complex is contacted with a second oligonucleotide probe that comprises a label and is capable of being ligated to the interrogation probes contained within the hybridization complex. This method also comprises providing means to ligate the second labeled oligonucleotide probe to the interrogation probe within the hybridization complex and then detecting the optical signals from the set of immobilized probes in real-time. One or more annealing-ligating-detecting-denaturing cycles are performed, with each cycle increasing the number of extended probes in arithmetic progression and involving the following steps:

(i) providing a first temperature for the formation of the hybridization complex;

(ii) providing a second temperature for ligase-catalyzed ligation of interrogation probe and the second labeled probe to occur, wherein ligation is associated with a change in optical signature of beads associated with the ligated probe;

(iii) imaging and/or recording optical signals from the probes; and (iv) providing a third temperature for denaturing all hybridization complexes.

Objects, features and advantages of the invention will be more clearly understood when taken together with the following detailed description which will be understood as being illustrative only, and the accompanying Figures.

DESCRIPTION OF THE FIGURES

FIG. 4 is a DNA sequence showing polymorphic markers within exon 7 of the CFTR gene (capital letters indicate known polymorphisms).

FIG. 5a is a DNA sequence showing polymorphic markers within exon 10 of CFTR gene.

FIG. 5b is an illustration of probes designed for SNP identification within exon 10 of the CFTR gene.

DETAILED DESCRIPTION

Figure 1:
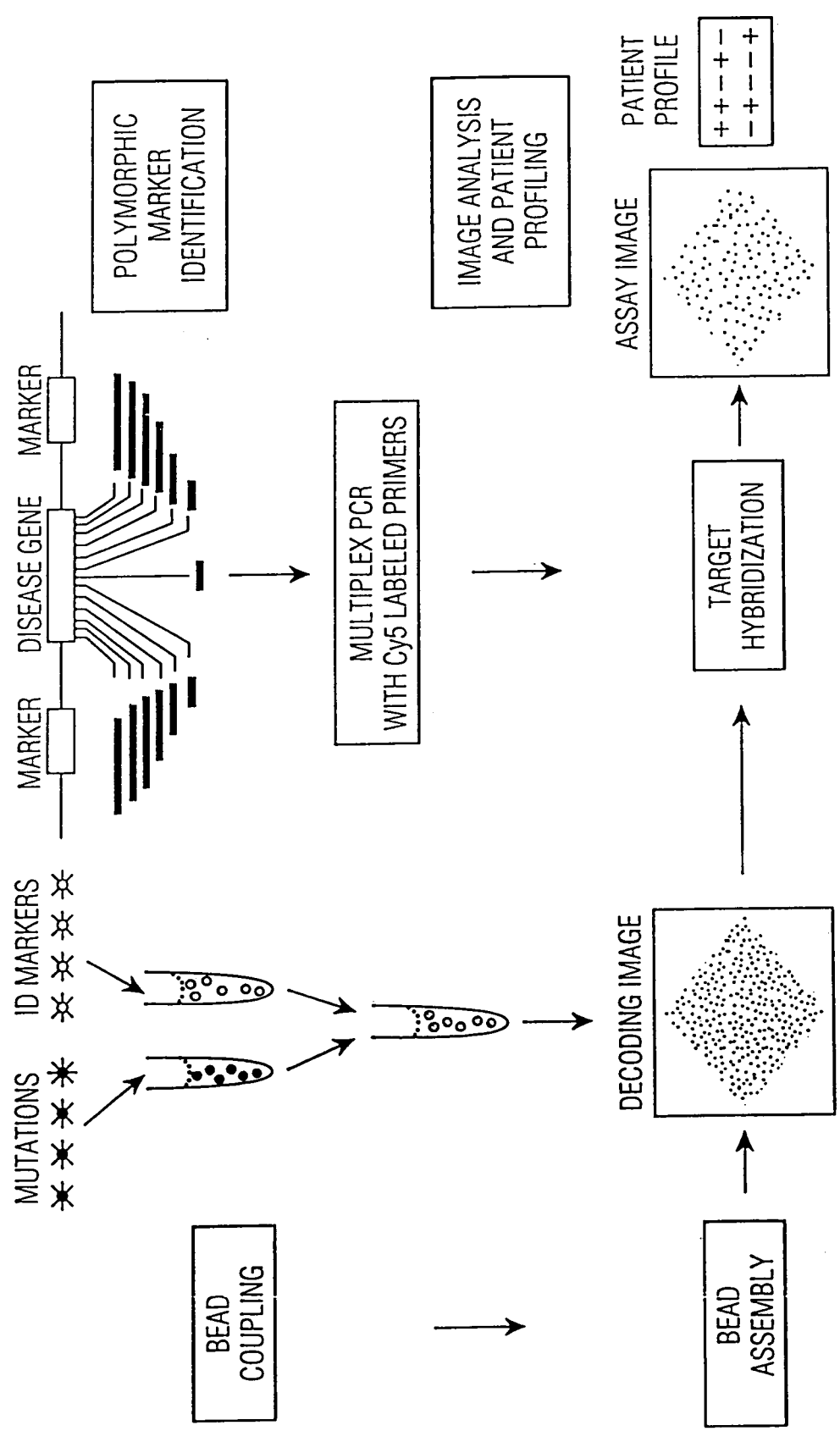
FIG. 1 is an illustration showing a protocol for creating an embedded genetic ID.

The genetic profiling of patients plays an increasingly important role, not only in basic and applied clinical research, but also in the diagnosis of disease and in the assessment of predisposition to disease. A safe, reliable genetic testing protocol preferably will incorporate all relevant information relating to patient identification within individual tests. The present invention provides methods and compositions for linking the genetic profile obtained from the analysis of a patient's sample to a patient's identity. This correlation between a patient's genetic profile and identity is established concurrently with the genetic test or any diagnostic or prognostic test, on the basis of recording a genetic fingerprint or molecular identifier (ID).

The methods of the present invention are useful in the prevention of mishandling, mislabeling and switching of samples in the course of genetic testing. These methods are useful in paternity and maternity testing, immigration and inheritance disputes, zygosity testing in twins, tests for inbreeding, evaluation of the success of bone marrow transplants, identification of human remains, and forensic testing such as those involving semen or blood. This invention prevents or corrects identification errors associated with mishandling, mislabeling and switching of samples by incorporating a genetic fingerprint or molecular identifier into the record of the genetic or other test, obtained, for example in the form of an image as elaborated herein. In this way, an unambiguous link between that record and the patient's identity is established. The molecular identifier may serve to track and to confirm the identity of the sample, thereby providing a means for authentication. The methods of the present invention provide compositions and methods to create a genetic ID, also referred to herein as an ID, concurrently with the completion of a genetic or other diagnostic or prognostic test. In cases of analyzing genetic loci such as CFTR that contain multiple mutations and widely dispersed markers, the present invention provides the means of recording ID markers located within the targets already amplified for the purpose of genetic analysis. In analyses wherein the genetic loci contain only few mutations, ID markers located in other genomic regions can be amplified by providing additional primers.

One widely used method of genetic fingerprinting involves the analysis of polymorphisms in a number of repeated sequence elements within certain loci. To facilitate the integration of repeated sequence polymorphisms, methods are provided herein for an array format of identity testing by STR/VNTR analysis. The methods of this invention minimize the number of steps required for sample handling and processing, thereby minimizing the possibility that the measurement process influences the results, a potential concern in the development of databases for patient identification. Although the genetic fingerprinting methods disclosed herein are particularly useful in providing patient identity in the context of genetic profiling, they also may be used in connection with other genetic analysis, such as genotyping, haplotyping or HLA molecular typing. The methods of the present invention also find utility in the context of genetic authentication performed independently of genetic analysis.

Furthermore, by assigning an ID to a particular sample container or carrier, the methods of the present invention create an unambiguous link between the carrier ID and the genetic ID, thereby not only minimizing the possibility of error in sample handling but also enabling verification of assay results. Carrier ID and genetic ID can be linked to a database for data corroboration and authentication of patient identity.

The use of a set of DNA fragments of known sequence as external labels as described in this invention is advantageous over the prior art in at least two respects. First, the determination of the tag, and hence the identification of the tagged sample, can be performed concurrently with the genetic analysis of interest using methods such as hybridization, elongation and ligation. Second, the resulting sample ID generally will be embedded in the image or data record produced by the genetic analysis. That is, the sample ID and the results of the genetic analysis remain linked. In contrast, tag identification by methods of the prior art generally require completion of a separate analytical procedure such as electrophoresis for the determination of DNA fragment lengths of the external labels, in addition to the genetic test itself.

As used herein, the term "polymorphism" refers to a sequence variation in a gene, and "mutation" refers to a sequence variation in a gene that is associated or believed to be associated with a phenotype. The term "gene" refers to a segment of the genome that codes for a functional product protein control region. Polymorphic markers used in accordance with the present invention for patient identification may be located in coding or non-coding regions of the genome. The term "patient," as used herein refers to an individual providing a test sample from which target nucleic acids are obtained for the purpose of genetic testing.

The terms "ID", "ID marker", and "marker" are used herein interchangeably to refer to internal markers and external markers whose high variability renders them suitable as a molecular identifier of a particular individual. For the purposes of this invention, internal markers, specifically including genetic ID markers for DNA fingerprinting, can be "intrinsic" markers which are located within the gene of interest or can be non-intrinsic, or "extrinsic" markers.

Internal markers include SNPs, STRs, VNTRs and other polymorphic sites within a genomic locus. External markers include chemical, fluorescent, magnetic, molecular and other tags that generally can be incorporated into the sample at the time of sample collection. They are useful in uniquely associating the results obtained in a genetic or other test such as prognostic and diagnostic tests with the identity of the patient. Examples of external-markers include biological labels such as tags composed of oligonucleotides, peptide nucleic acids, DNA, RNA, proteins, ABO blood type and the like, and chemical labels such as optically active particles, dyes and the like.

A collection of random DNA sequence tags, such as those constructed for use in certain hybridization assays represent a class of external markers providing a very large encoding capacity. For example, a recently published set of 164 sequence tags (http://waldo.wi.mit.edu/publications/SBE-TAGS), derived from the genome of bacteriophage λ, would provide $2^{164}$ distinct combinations. In a preferred embodiment, the presence or absence in a given sample of each of the DNA sequence tags selected from a library is determined by providing an identification array of color-encoded beads, wherein beads of each type display an oligonucleotide probe that uniquely matches one of the sequence tags. The set of signals from beads within the identification array, averaged over beads of the same type, constitutes a molecular barcode of the patient sample.

Inorganic fluorescent nanoparticles synthesized by methods known to the art to emit light in response to single wavelength excitation at wavelengths determined by the particle size, represent another class of external markers. The presence in the sample of a specific subset of nanoparticle tags is determined by spectral analysis of the sample concurrently with the completion of the DNA analysis of interest. Two types of inorganic nanoparticle labels have been described in prior art, namely semiconductor Q-dot (Quantum Dot) particles and RLS (Resonant Light Scattering) metal nanoparticles. Quantum dots are nanometer ($10^{-9}$ meter) scale particles made from semiconductor materials such as cadmium selenide (CdSe), cadmium telluride (CdTe), or indium arsenide (InAs). Their composition and small size (a few hundred to a few thousand atoms) give these dots extraordinary optical properties that can be readily customized by changing the size or composition of the dots. Quantum dots absorb light, then quickly re-emit the light at a different wavelength. Although other organic dyes and inorganic materials exhibit this phenomenon, quantum dots have the advantage of being bright and non-bleachable with narrow, symmetric emission spectra, and have multiple resolvable colors that can be excited simultaneously using a single excitation wavelength. (Bruchez et al., "Semiconductor Nanocrystals as Fluorescent Biological Labels, Science, 281, 2013 (1998), Alivisatos, "Semiconductor Clusters, Nanocrystals, and Quantum Dots Science, 271, 933 (1996)).

Resonance Light Scattering Technology (RLS Technology) is based on "nano-sized" metal (for example gold or silver) colloidal particles that radiate energy in the form of scattered light when illuminated by a simple white light source. The monochromatic light signal generated by a single RLS Particle is $10^4$ to $10^6$ times greater than the signal obtained from the most sensitive fluorophore and hence these nanoparticles can act as ultra-sensitive biological labels in a wide variety of analytical bioassay and test formats. (Yguerabide, J. Analytical Biochemistry, 262, 137-156 (1998), Yguerabide, J. Analytical Biochemistry, 262, 157-176 (1998)).

To use an external marker according to this invention, a sample such as a blood, sputum, hair or bone marrow sample is collected. An external marker is incorporated as part of the sample and remains incorporated or otherwise associated with the sample while the sample undergoes processing and analysis. Such markers can be incorporated in the context of assays involving population carrier screening, genotyping, haplotyping or protein analysis such as profiling of cytokines, antigens, or antibodies in serum.

In certain embodiments, one or more external markers can be used in lieu of one or more internal markers. In other embodiments, one or more external markers can be used in combination with one or more internal markers, thus providing an additional means for sample identification and authentication. External markers also can be incorporated in an assay contained in a cartridge designed and provided for collection and/or storage of a patient sample, thereby creating a physical linkage between the sample, the assay container or carrier and the genetic test.

The target sequence or target nucleic acid for genetic testing and for genetic fingerprinting may be a portion of a gene, a regulatory sequence, genomic DNA, cDNA, and RNA (including mRNA and rRNA). Genomic DNA samples are usually amplified before being brought into contact with a probe. Genomic DNA can be obtained from any tissue source or circulating cells (other than pure red blood cells). For example, convenient sources of genomic DNA include whole blood, semen, saliva, tears, urine, fecal material, sweat, buccal cells, skin and hair. Amplification of genomic DNA containing a polymorphic site generates a single species of target nucleic acid if the individual from which the sample was obtained is homozygous at the polymorphic site, or two species of target molecules if the individual is heterozygous. RNA samples also are often subject to amplification. In this case, amplification is typically preceded by reverse transcription. Amplification of all expressed mRNA can be performed as described in, for example, WO 96/14839 and WO 97/01603 which are hereby incorporated by reference in their entirety. Amplification of an RNA sample from a diploid sample can generate two species of target molecules if the individual providing the sample is heterozygous at a polymorphic site occurring within the expressed RNA, or possibly more if the species of the RNA is subjected to alternative splicing. Amplification generally can be performed using the PCR methods known in the art. Nucleic acids in a target sample can be labeled in the course of amplification by inclusion of one or more labeled nucleotides in the amplification mixture. Labels also can be attached to amplification products after amplification (e.g., by end-labeling). The amplification product can be RNA or DNA, depending on the enzyme and substrates used in the amplification reaction.

Tandem repeats, such as short tandem repeats (STRs) for example, can be used as genetic ID markers. Frequently, genetic loci of interest to genotyping and related genetic testing contain a repeated sequence composed of a number of repeated sequence elements that is highly variable between individuals. In one aspect of the invention wherein the marker is a tandem repeat, the number of tandem repeats in a target nucleic acid sequence may be determined by parallel interrogation as elaborated herein.

In one preferred embodiment, in order to score mutations in the course of genetic testing, probe pairs generally are designed for each variable target site of interest. Both probes in a pair are complementary to the target nucleic acid sequence except at the mutation site where at least one probe in the pair is complementary to the target. Probes are of sufficient length to allow hybridization to the target and are preferably 10 to 50 bases long, more preferably 10 to 20 bases long. The probes also may be attached to a solid support by a linker. Mutation analysis involves interrogation of one or more target sequences and may be performed in a multiplexed format that facilitates high-throughput screening. For example, probes directed to different target sequences may be arranged in a planar, random array by attaching probes to encoded beads, as described herein. In another example, different sub-arrays on the same substrate (e.g., a silicon electrode) may be formed, with both bead encoding and location of bead subarray providing information about the identity of the probes located on individual beads. As with the analysis of repeated sequences, parallel interrogation involves the formation of hybridization complexes between target and sequence-specific probes. In a preferred embodiment, probe elongation provides the means for the direct labeling of elongation products by incorporation of fluorescently labeled dNTPs including, but not limited to, methods that combine elongation and on-chip temperature cycling. Labeled elongation products are detected by imaging as described herein.

In a preferred embodiment of this invention, sets of elongation probes capable of "priming" the elongation reaction are immobilized on solid phase carriers in a way to preserve their identity and to reduce ambiguities in the identification of elongated products. For example, this can be achieved by spatially separating different probes and/or by chemically encoding probe identities.

When the probes are contacted with target strands under conditions permitting formation of hybridization complexes, the interrogation site located at or near the 3' terminus of each probe will align with the target generally in one of two configurations, namely either in a "repeat-interior" configuration or in a "repeat-exterior" configuration. In the former, the interrogation site is juxtaposed to a site within the target's repeated sequence; in the latter, it is juxtaposed to a site within the target's leading sequence.

Figure 13:
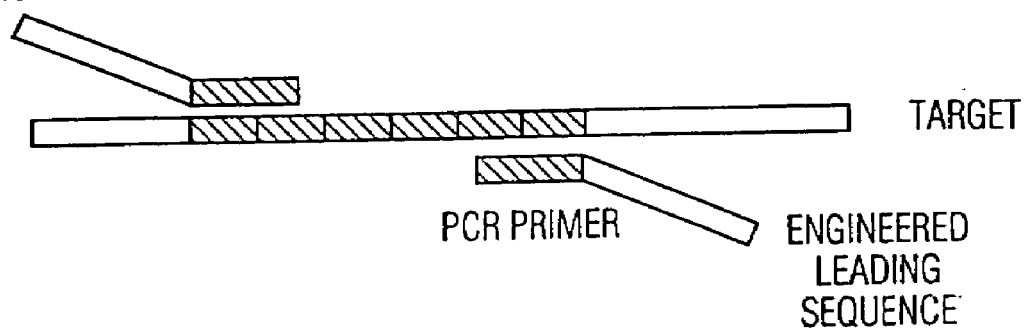
FIG. 13 is an illustration of hybrid primers for STR polymorphism analysis.

Probes are usually designed with complementary trailing and leading sequences to the desired genomic regions. To make universal trailing and leading sequences, hybrid primers can be designed with sequences that will be part of the amplified product. For example, forward and reverse PCR primers can be designed to contain at their respective 5' ends a GC rich tag. PCR amplification of genomic DNA introduces this tag at the 5' end of the product (FIG. 13). Oligonucleotide probes are then designed to contain a 5' anchor sequence that is complementary to the primer tag. This design flexibility facilitates correct probe alignment to the amplified target to minimize slippage (i.e. the target hybridizing at several different places) and enhances discrimination in assays. For example, the trailing sequence is designed in such a way to start with a nucleotide that is not present in the repeat sequence (for di- and tri-nucleotide repeats) and can be detected by single base extension.

The step of interrogating the repeated sequence of a target by a set of interrogation probes containing variable numbers of repeats is designed to assign to each probe one of two values corresponding to one of these two configurations, namely matched, (numerically represented by 1), or non-matched, (numerically represented by 0). The binary sequence of interrogation results produced from a set of probes directed against a repeated sequence polymorphism determines the number of target repeats within that polymorphism. As elaborated herein in numerous examples, many variations of probe construction and detection methods are possible including, but not limited to, direct hybridization with detection by way of fluorescence energy transfer, and template mediated probe elongation including single base extension or ligation.

In certain embodiments, the probe sequence may be constructed to contain an offset sequence, located on the 5' side of the first probe repeat, with the offset sequence matching the first one or more (but not all) nucleotides of the target repeat. Annealing of an offset-containing probe to the target in perfect alignment again produces a hybridization complex in one of two possible configurations. In the first of these, probe repeats are displaced relative to target repeats by an amount equal to the size of the offset in the probe's 3' direction, so that the 3' terminus of the probe sequence is aligned with an interior position of one of the target repeats. In the second configuration, the 3' terminus of the probe sequence is aligned with a position within the leading sequence, that position being determined by the size of the offset.

For each repeated sequence polymorphism of interest, a set of probes can be constructed to contain the same (optional) anchor sequence and the same (optional) offset sequence, but successively higher numbers of repeats, such that the set of probes spans the range of possible target repeats as elaborated herein. In one embodiment, probes can be designed to contain 5'- and 3'-anchor sequences that are complementary to the target's trailing and leading sequences so as to stabilize desirable alignments of probe and target. Leading and trailing sequences of desired composition may be introduced at the point of amplification of a patient's DNA by PCR methods known in the art (Innis et al, Academic Press, San Diego, Calif. (1990), Mattila et al., Nucleic Acid Research, 4967 (1991)). Leading and trailing sequences can be switched to determine the repeats on the complementary DNA strand.

In other embodiments, oligonucleotide probes containing neither 5'- nor 3'-anchor sequences can be used in competitive hybridization. In one such embodiment, a labeled or unlabeled target is first permitted to form a hybridization complex with a "blocking" DNA strand designed to contain a sufficiently large number of repeats so as to exceed the largest expected number of target repeats. In this hybridization complex, all target repeats are therefore in a duplex configuration. A solution of this "blocked" target is now placed in contact with an array of encoded beads displaying probes with varying numbers of repeats. The reaction mixture is incubated to permit probes to compete with the blocking strand for binding to the target repeats. In this design, only those probes that contain a number of repeats matching or exceeding the number of target repeats will displace (a portion of) the blocking strand from the target and thereby acquire assay signal. Washing at increasing stringency, as well as adjustment of annealing temperature as described herein, enhances the level of discrimination.

In another preferred embodiment, assay images are recorded at increasing temperatures and signals are recorded as a function of increasing temperature. Successive peaks in the intensity-versus-temperature plots for all probe-target hybridization complexes indicate the respective melting temperatures, with probes containing a number of repeats that match or exceed the number of target repeats having the highest melting temperature. Differently colored labeled targets can be analyzed within the same reaction.

A target that forms a hybridization complex with immobilized probes can be visualized by using detection methods previously described herein. For example, probes annealed to target strands can be elongated with labeled dNTPs, such that extension occurs when the probe perfectly matches the number of repeats in the target. Several other configurations for generating positive assay signals may be readily constructed.

As described for sequence-specific probes in general, probes for parallel interrogation repeated sequences may be immobilized on solid supports via a linker moiety, use of which is well known in the art. As a general rule, probes should be sufficiently long to avoid annealing to unrelated DNA target sequences. The length of the probe may be about 10 to 50 bases, more preferably about 15 to 25 bases, and even more preferably 18 to 20 bases. In a multiplexed assay, one or more solution-borne targets are then allowed to contact a multiplicity of immobilized probes under conditions permitting annealing and elongation reactions. Thus, the present invention offers advantages over the existing methods of analyzing repeated sequence polymorphisms by gel electrophoresis, a methodology which is not adaptable to high throughput operation.

The present invention also includes methods for the parallel interrogation of single nucleotide polymorphisms and single site mutations as well as for detecting other types of mutations and polymorphisms such as multiple nucleotide polymorphisms (for example double, triple and the like), as well as small insertions and deletions commonly observed and useful for genetic testing.

To minimize labor, materials, and time to completion required for analysis, it is desirable to amplify and to analyze multiple loci simultaneously in a single reaction. Multiplexed amplification methods are particularly useful in the analysis of genetic diseases including, among others, Duchenne Muscular Dystrophy, Lesch-Nyhan Syndrome, and Cystic Fibrosis. In addition, several autoimmune diseases (such as Diabetes mellitus) have been linked to polymorphisms in the Human Leukocyte Antigen (HLA) system. The polymorphic loci of the HLA complex exhibit strong linkage disequilibrium, such that particular haplotypes occur together on the chromosome more often than would be predicted. Susceptibility to insulin-dependent diabetes mellitus (IDDM) has been found to be associated with particular class II alleles encoded by DQ loci. The loci DQ alpha are used for molecular typing and can be used for simultaneous analysis involving disease sequencing and molecular typing.

Genetically defined mitochondrial diseases, most of which are caused by mutations in mitochondrial (mt) DNA, provide another example. The average human cell contains thousands of mtDNA molecules, which are closed circular molecules of 16,586 nucleotide pairs that code for 37 genes, 13 oxidative phosphorylation (OXPHOS) polypeptides, rRNAs and 22 tRNAs. The mtDNA molecules have a much higher mutation rate than does the nuclear genome.

Figure 8:
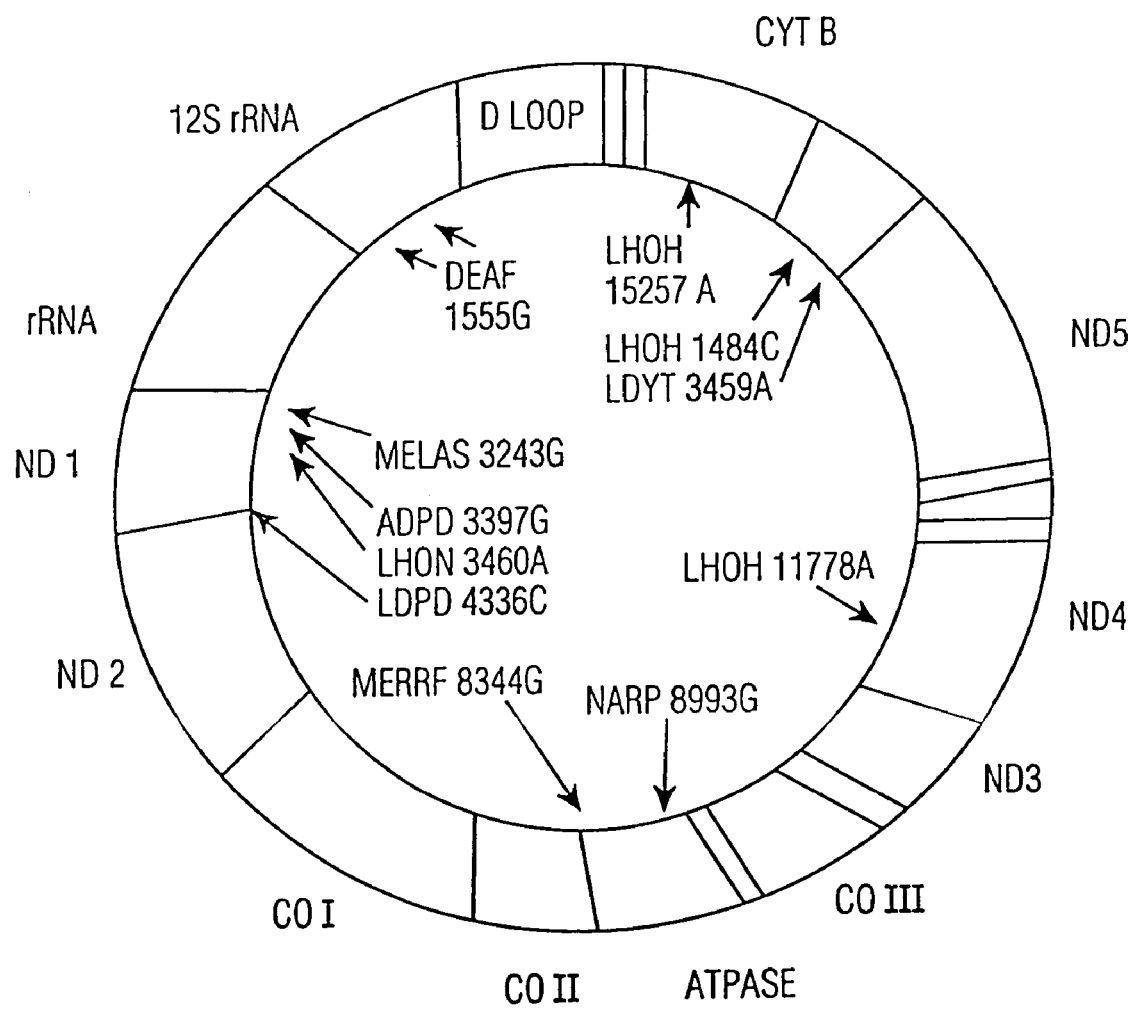
FIG. 8 is an illustration showing a mitochondrial genome with genes on outside of the circle and various disease causing mutations and polymorphisms inside of the circle.

Several of mtDNA mutations have been linked to degenerative diseases of brain, heart, skeletal muscle and kidney (FIG. 8). Mitochondrial encephalomyopathies form a genetically heterogeneous group of disorders associated with impaired oxidative phosphorylation. Patients may exhibit a wide range of clinical symptoms from muscle weakness to vision loss and brain degenerative disorders, for which there currently is no curative treatment. Base substitutions and rearrangement mutations occurring in the mitochondrial genome are correlated with ocular myopathies, Kearn-Sayre or Pearson syndromes and adult-onset diabetes mellitus. Mitochondrial diseases result from mutations in the female germline or acquired mutations. Base substitution mutations in ATP synthase have been associated with muscle weakness, ataxia, retinitus pigmentosa (NARP), Leigh syndrome, central vision loss (LHON) dystonia, and MELAS. Three mtDNA mutations have been identified to be associated with Alzheimer's and Parkinson's diseases.

Several polymorphic markers have been identified in mtDNA and have been used extensively in studies of population genetics. Most of these markers are located within, and can be co-amplified with, genes containing disease-causing mutations Specifically, 32 sequence polymorphisms, located within the tRNA gene, are suitable as individual ID markers which can be embedded within the mutation profile. (Garboczi, et al, Mol. Cell BioChem 107: 21-29 (1991)).

The methods of the present invention involve the concurrent interrogation of target nucleic acid sequences as well as genetic ID markers. This can be accomplished by providing two or more sets of nucleic acid probes, such as DNA or RNA in single-stranded or double-stranded form, or nucleic-acid like structures with synthetic backbones such as peptide nucleic acids. According to the invention, the first set of probes is designed to be complementary to a target nucleic acid sequence of interest, and the second set of probes is designed to be complementary to one or more designated ID markers. These first and second sets of probes can be attached to solid phase carriers such as, for example, a chip, wafer, slide, membrane, particle, bead, or any surface which would be compatible with the assay considered.

As used herein, the terms "bead," "microsphere," "microparticle," and "particle" are used interchangeably. Bead composition may include, but is not limited to, plastics, ceramics, glass, polystyrene, methylstyrene, acrylic polymers, paramagnetic materials, carbon graphite, titanium dioxide, latex or cross-linked dextrans such as sepharose, cellulose, nylon, cross-linked micelles and polytetrafluoroethylene.

Beads may be associated with a physically or chemically distinguishable characteristic. For example, beads may be stained with sets of optically distinguishable tags, such as those containing one or more fluorophore or chromophore dyes distinguishable by excitation wavelength, emission wavelength, excited-state lifetime or emission intensity. Optically distinguishable dyes combined in certain molar ratios may be used to stain beads in accordance with methods known in the art. Combinatorial color codes for exterior and interior surfaces are disclosed in International Application No. PCT/US98/10719, incorporated herein by reference. Beads capable of being identified on the basis of a physically or chemically distinguishable characteristic are said to be "encoded."

The detection of the chemically or physically distinguishable characteristic of each set of beads and the identification of optical signatures on such beads generated in the course of a genetic or other test (such as diagnostic or prognostic test) using such beads may be performed by respectively recording a decoding image and an assay image of a set or array of such beads and comparing the two images. For example, in certain embodiments, a system with an imaging detector and computerized image capture and analysis apparatus may be used. The decoding image is obtained to determine the chemical and/or physical distinguishable characteristic that uniquely identifies the probe displayed on the bead surface. In this way, the identity of the probe on each particle in the array is provided by the distinguishable characteristic. The assay image of the array is obtained to detect an optical signature produced in the assay as elaborated herein below.

In addition to being encoded, beads having specific oligonucleotide probes or primers may be spatially separated in a manner such that the bead location provides information about bead and hence about probe or primer identity. In one example, spatial encoding may be provided by placing beads in two or more spatially separate subarrays.

In a preferred embodiment, beads can be arranged in a planar array on a substrate before decoding and analysis. Bead arrays may be prepared by the methods disclosed in PCT/US01/20179, incorporated herein by reference in its entirety. Bead arrays also may be formed using the methods described in U.S. Pat. No. 6,251,691, incorporated herein by reference in its entirety. For example, light-controlled electrokinetic forces may be used to assemble an array of beads in a process known as "LEAPS", as described in U.S. Pat. No. 6,251,691. Alternatively, if paramagnetic beads are used, arrays may be formed on a substrate surface by applying a magnetic field perpendicular to the surface. Bead arrays also may be formed by mechanically depositing the beads into an array of restraining structures (e.g., recesses) at the surface of the substrate. In certain embodiments, the bead arrays may be immobilized after they are formed by using physical means, such as, for example, by embedding the beads in a gel to form a gel-particle film.

An example of multiplexed molecular analysis using random encoded bead arrays is provided by genetic analysis and testing of ABO (and RH) blood type. In this embodiment, encoded bead arrays are assembled in separate locations on a given chip to permit concurrent genetic analysis and testing. This analysis is performed by displaying, on encoded beads, individual antigens corresponding to ABO-type and RH-factor and assembling these beads into an array which is then used to determine the antibody profile in the patient's serum in a multiplexed immunoassay.

ABO blood typing is based on the fact that humans and most vertebrates carry complex oligosaccharides attached to serine side chains of certain membrane proteins. Oxygen-linked polysaccharides complexes frequently are exposed on the outer surface of human cells and elicit a specific immune response when the cell carrying them is injected into individuals that do not contain the same cell surface antigens. This pattern of adverse immune response in mismatched individuals forms the basis of ABO-blood group classification, wherein individuals of the same blood type can accept blood transfusions from one another, whereas individuals with different blood types cannot. Additional blood types are defined on the basis of compatibility or incompatibility with rhesus factors and serves to correlate blood type with distinct individual genetic fingerprint.

Blood type reflects the expression of two genes that determine A and B blood type. The A-gene encodes a glycosyltransferase that catalyzes the addition of a terminal N-acetyl-galactosamine (Gal Nac) residue to a core polysaccharide, while the B gene encodes a similar enzyme that adds a galactose (Gal) residue to the same site. When A and B genes are present, both structures are found, but when only O genes are present, the site on the oligosaecharide is left exposed. Cells of an AA or AO individual carry A-antigen, cells of a BB or BO individual carry B antigen, while cells of an AB individual carry both A and B antigens and cells of an OO individual carry neither antigen.

Thus, biochemical markers which form part of the patient's medical record, such as the set of cell surface antigens that define the blood type of an individual, can be used to link a genetic profile to a patient's identity. This information can be obtained by on-chip genetic testing and can be linked to a concurrently recorded biochemical ID marker which in turn can be cross-referenced with existing patient records to ensure authenticity.

According to the methods of this invention, the concurrent interrogation of a target nucleic acid sequence and a genetic fingerprint can be performed by first identifying a genetic ID marker or plurality of markers of interest, as elaborated in Examples herein, and then designing a plurality of oligonucleotide probes: a first set directed to target nucleic acid sequences of interest, and a second set directed to the marker or markers of interest. That is, the first, set of probes is used in an assay designed for genetic testing or profiling and the second set of probes is used in the determination of a molecular fingerprint, concurrently with the genetic testing. When intrinsic markers are used, the intrinsic markers are coamplified with other designated mutations of polymorphisms in a target sequence. When extrinsic markers are used, separate primer sets for separate but contemporaneous amplification may be required.

Interrogation of an amplified target nucleic acid sequence containing polymorphic sites or plurality of such sequences for genetic profiling as well as genetic ID markers involves forming a hybridization complex by annealing targets to encoded, sequence-specific oligonucleotide probes to determine the degree of sequence complementarity between probes and target fragments.

Interrogation of target genes and markers may be accomplished in various ways within the scope of the invention. For example, in one embodiment (referred to herein as "direct hybridization"), fluorescently labeled target fragments may be used to impart a detectable optical signature, such as fluorescence, to the hybridized probe-target complex. A labeled target is readily produced by prior target amplification with labeled primers. In another embodiment, direct hybridization can employ a labeled detection probe. For example, fluorescence energy transfer may be used to create a detectable optical signature via the formation of three-member hybridization complexes, as elaborated in the Examples provided herein. In a further embodiment, the target sequence composition can be determined from the signal pattern of enzyme-mediated ligation and elongation reactions applied to the probe sets provided. In elongation-mediated detection, a polymerase-mediated elongation reaction produces a signal pattern reflecting the elongation or extension of sequence-specific probes that are designed to function as primers. Signal patterns generated by any of these methods of the present invention contain a unique individual genotype along with a "fingerprint."

As used herein, "hybridization" refers to the binding, annealing, duplexing, or hybridizing of a first nucleic acid molecule preferentially to a particular second nucleotide molecule. The stability of a hybridization complex varies with sequence composition, length and external conditions. Hybridization methods include those that rely on the control of stringency in reaction conditions to destabilize some but not all hybridization complexes formed in a mixture. Using these methods, it is possible to distinguish complete complementarity from partial complementarity between probe and target sequences that form a hybridization complex.

To facilitate detection, hybridization complexes can be modified to contain one or more labels. These labels can be incorporated by any of a number of means well known to those skilled in the art. Detectable labels suitable for use in the present invention include any composition detectable by spectroscopic, photochemical, biochemical, immunochemical, electrical, optical, or chemical means. Useful labels in the present invention include high affinity binding labels such as biotin for staining with labeled streptavidin or its conjugate, magnetic beads, fluorescent dyes (for example, fluorescein, Texas red, rhodamine, green fluorescent protein, and the like), radiolabels (for example $^3$H, $^{125}$I, $^{35}$S, $^{14}$C, or $^{32}$P), enzymes (for example horseradish peroxidase, alkaline phosphatase and others commonly used in an ELISA), epitope labels, and colorimetric labels such as colloidal gold, colored glass or plastic beads (for example polystyrene, polypropylene, latex, and the like). Means of detecting such labels are well known to those of skill in the art. Thus, for example, radiolabels can be detected using photographic film or scintillation counters, and fluorescent markers can be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label. One method uses colloidal gold as a label that can be detected by measuring light scattered from the gold. The label can be added to the amplification products prior to or after the hybridization.

"Direct labels" are detectable labels that are directly attached to, or incorporated into, the nucleic acids prior to hybridization. In contrast, "indirect labels" are affixed to, or incorporated into the hybridization complex following hybridization. Often, the indirect label is attached to a binding moiety that has been attached to the amplified nucleic acid prior to hybridization. Thus, for example, the amplified nucleic acid can be biotinylated before hybridization. After hybridization, an avidin or streptavidin conjugated fluorophore will bind the biotin-bearing hybrid duplexes, providing a label that is easily detected.

Means for detecting labeled nucleic acids hybridized to probes in an array are known to those skilled in the art. For example, when a colorimetric label is used, simple visualization of the label is sufficient. When radiolabeled probes are used, detection of the radiation (for example, with photographic film or a solid state detector) is sufficient. Detection of fluorescently labeled target nucleic acids can be accomplished by means of fluorescence microscopy. An array of hybridization complexes can be excited with a light source at the excitation wavelength of the particular fluorescent label of choice and the resulting fluorescence at the emission wavelength detected. The excitation light source can be, for example, a laser appropriate for the excitation of the fluorescent label.

In a preferred embodiment, the interrogation step involves the elongation of target-annealed probes. This reaction, catalyzed by a polymerase, produces an elongated hybridization complex by appending to the probe sequence one or more nucleoside triphosphates in an order reflecting the composition of the target sequence in the existing hybridization complex. In order for this elongation reaction to proceed, the probe length must contain a terminal elongation initiation ("TEI") sequence. The TEI sequence in turn contains an interrogation site which preferably coincides with the 3' terminus but also may be displaced from the 3' terminus by 3-4 bases within the primer sequence. Elongation proceeds if the composition of the interrogation site matches that of the designated target site.

A method of extending the recessed 3' end of a double-stranded DNA by addition of selected deoxynucleoside triphosphates (dNTPs) in order to copy the protruding single complementary strand and to determine the specificity of the reaction has been reported in the art (Wu, Proc. Natl Acad. Sci, 57(1):170-171 (1967), Wu, J. Mol. Biol, 14:35(3): 523-37 (1968)). They incorporated one dNTP at a time, trying up to four dNTPs per position and using radioactively labeled dNTP's to detect successful incorporation.

In contrast to the prior art, the present invention provides a parallel format of repeated sequence analysis in which all extension reactions occur simultaneously on multiple copies of double stranded DNA formed by site-specific interrogation probes and a target. In some embodiments of this invention, to facilitate the parallel detection of successful extensions, optical signatures produced by the extension reaction are imaged.

In one embodiment of the invention, two or more probes may be provided for interrogation of a specific designated site, these probes being constructed to anticipate polymorphisms or mutations at the interrogation site and non-designated polymorphic sites within a certain range of proximity of the designated polymorphic site. In a preferred embodiment, this multiplicity of probe sequences contains at least one probe that matches the specific target sequence in all positions within the range of proximity to ensure elongation.

Furthermore, in some embodiments of this invention, a covering probe set is used. A covering probe set, (described in U.S. Provisional Patent Application 60/364,416 which is hereby incorporated by reference in its entirety) contains probes permitting the concurrent interrogation of a given multiplicity of designated polymorphic sites within a nucleic acid sequence and comprises, for each site, at least one probe capable of annealing to the target so as to permit, on the basis of a subsequent elongation reaction, assignment of one of two possible values, "matched" (elongation) or "unmatched" (no elongation) to that site.

The covering probe set associated with each designated site may contain two or more probes differing in one or more positions. In certain embodiments, the probe sequence may contain universal nucleotides capable of forming a base-pair with any of the nucleotides encountered in DNA. In certain embodiments, probes may be attached to encoded microparticles, and specifically, two or more different types of probes in a covering set may be attached to the same type of microparticle. The process of attaching two or more different types of probes to a bead is referred to as "probe pooling".

A mismatch in a single position within the TEI region, or a mismatch in three or more positions within the duplex anchoring ("DA") region (i.e., annealing subsequence) suffices to preclude elongation. Accordingly, the elongation of two probes displaying such differences in composition generally will produce distinct elongation patterns. All such probes can be multiplexed in a parallel elongation reaction as long as they are segregated, that is, individually encoded.

Probes displaying identical TEI subsequences and displaying DA subsequences differing in not more than two positions generally will produce elongation reactions at a yield (and hence signal intensity) either comparable to, or lower than that of a perfect match. In the first case, indicating tolerance of the mismatch, the set of alleles matched by the probe in question will be expanded to include those alleles displaying the tolerated mismatched sequence configurations within the DA region. In the second case, indicating only partial tolerance, three approaches are described herein to further elucidate the allele matching pattern. In the first approach, those probes displaying one or two nucleotide polymorphisms in their respective DA regions are included in the covering set, and information regarding the target sequence is obtained by quantitatively comparing the signal intensities produced by the different probes within the covering set. In the second approach, probes comprising separate TEI and DA regions joined by a tether are used to place the DA region farther away from the TEI region in order to avoid target polymorphisms. In the third approach, probes are optionally pooled in such cases offering only a modest expansion of the set of matched alleles.

While this method of accommodating or identifying non-designated polymorphic sites is especially useful in connection with the multiplexed elongation of sequence specific probes, it also may be used in mini-sequencing reactions (see e.g., Pastinen, et al. Genome Res. 7: 606-614 (1997), incorporated herein by reference).

In certain embodiments, the polymerase catalyzing primer elongation is a DNA polymerase lacking 3' to 5' exonuclease activity. Examples of such polymerases include T7 DNA polymerase, T4 DNA polymerase, ThermoSequenase and Taq polymerase. A reverse transcriptase may be used when the target comprises an RNA sequence. In addition to polymerase, nucleoside triphosphates can be added, preferably all four bases. For example dNTPs or analogues may be added. In certain other embodiments, ddNTPs may be added.

Successful probe extension may be indicated by a change in the optical signature of the solid phase carriers associated with the extended primers. This is accomplished by direct or indirect labeling methods well known in the art. (For a detailed review of methods of labeling nucleic acids and detecting labeled hybridized nucleic acids, see Laboratory Techniques in Biochemistry and Molecular Biology, Vol. 24, P. Tigson Ed., Elsevier, N.Y. (1993)).

In direct labeling, the extension reaction produces a product with a corresponding optical signature. In certain embodiments, fluorophore or chromophore dyes may be attached to one or more of the nucleotides added during extension so that the elongated primer acquires a characteristic optical signature. Successful extension has previously been described which involves the use of labeled deoxynucleoside triphosphates (dNTPs) such as Cye3-dUTP or dideoxynucleoside triphosphates (ddNTPs). (Wu, 1968, see above)

In indirect labeling, an optical signature is produced in additional steps performed subsequent to the elongation reaction. This invention also provides novel methods of providing optical signatures for detecting successful extension reactions, thus eliminating the need for labeled dNTPs or ddNTPs, which is advantageous because the efficiency of available polymerases in accommodating dNTPs or ddNTPs is reduced if the dNTPs or ddNTPs are labeled.

The methods of the present invention further include the formation of three-member hybridization complexes and their application to the parallel interrogation of tandem repeats, including, but not limited to methods that combine ligation and on-chip temperature cycling.

In one embodiment of the invention, the interrogation step utilizes the formation of a three-member hybridization complex. In addition to the target and the interrogating probe, this complex contains a modifying probe that is annealed to the target in a position immediately adjacent to the annealed interrogation probe. Optionally, the modifying probe may be ligated to the interrogating probe.

In one embodiment, a three-member hybridization complex is formed that includes an interrogating probe and a read-out probe that are designed to be a fluorescence energy transfer pair. The read-out probe sequence matches a selected subsequence of the target, covering one or more repeats adjacent to the 3' terminus of the target-annealed interrogation probe. In other words, the three-member hybridization complex will form only when the 3' terminus of the interrogation probe is aligned with a target site interior to the repeated sequence polymorphism. To permit the interrogation probe and the read-out probe within the three-member hybridization complex to form a fluorescence energy transfer pair, the interrogation probe is constructed to contain at or near its 3' terminus, a first fluorophore, referred to as the donor, and the read-out probe is constructed to contain, at or near its 5' terminus, a second fluorophore, referred to as the acceptor. When the donor and acceptor are annealed to the target, a gap of generally not more than 3-4 nucleotides separates the donor from the acceptor. Under these conditions, fluorescence energy transfer from donor to acceptor occurs when the three-member hybridization complex forms but does not occur when the three-member hybridization complex is not formed.

Figure 15A:
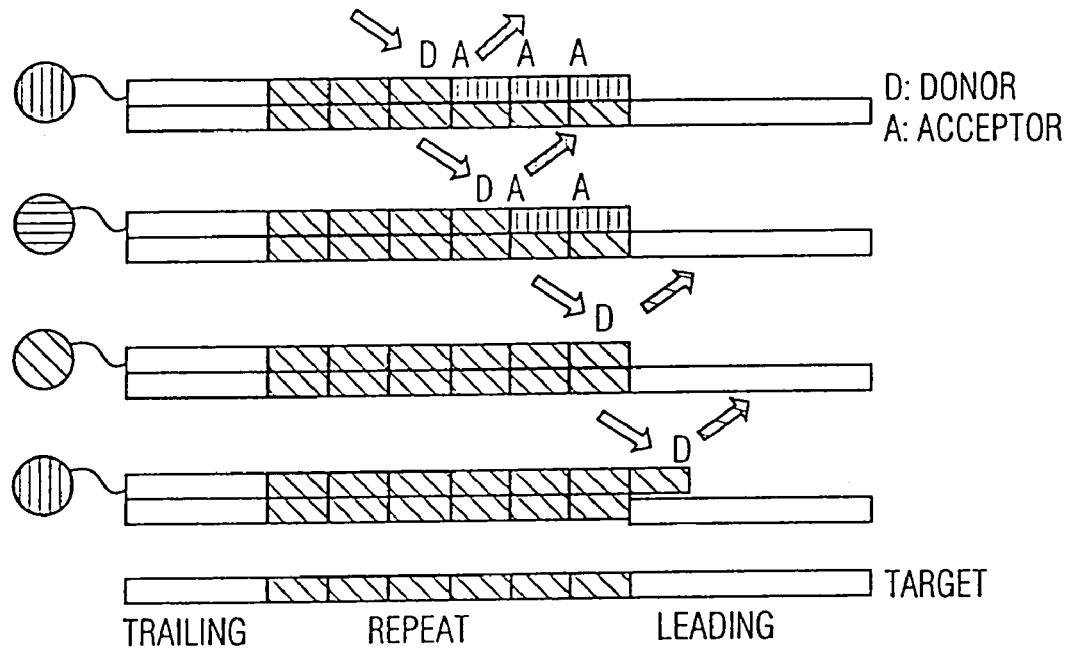
FIG. 15a is an illustration of fluorescence energy transfer with an interior interrogation probe.
Figure 15B:
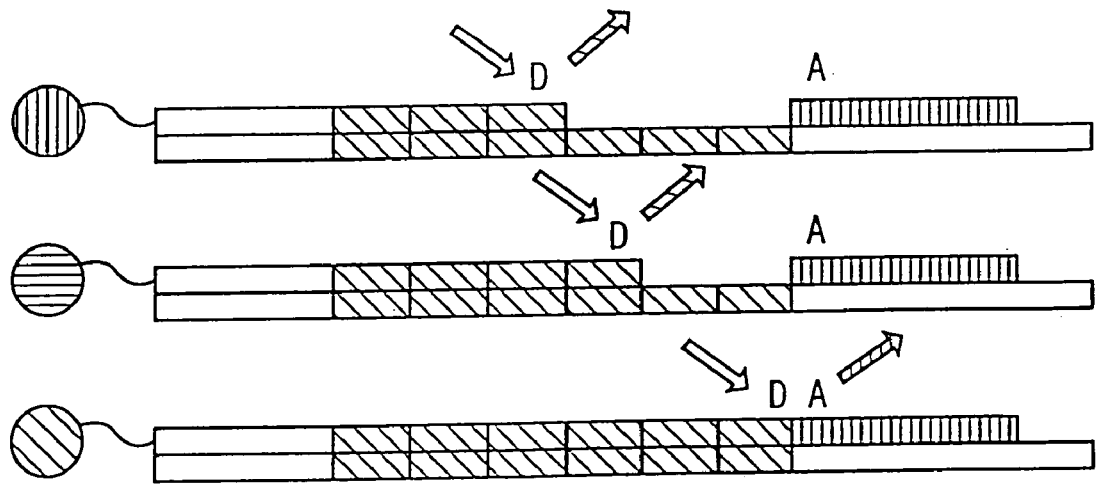
FIG. 15b is an illustration of fluorescence energy transfer with an exterior interrogation probe.

An example of fluorescence energy transfer is shown in FIGS. 15a and 15b. Two sets of oligonucleotide probes were designed to be complementary to a sequence in the amplified products just before the repeated sequence. In this design, a three-member hybridization complex is formed in such as way as to place only the interrogation probe containing the correct number of repeats into immediate proximity of the read-out probe, thereby permitting fluorescence energy transfer from donor to acceptor.

In this way, the "repeat-interior termination" and "repeat-exterior termination" configurations of the hybridization complex formed by interrogation probe and target are readily distinguished in a parallel interrogation assay using dual color detection. The former permits formation of a three-member hybridization complex and thus permits fluorescence energy transfer so that illumination at the excitation wavelength of the donor produces fluorescence at the emission wavelength of the acceptor. In contrast, the latter does not permit formation of the three-member hybridization complex so that illumination at the excitation wavelength of the donor produces fluorescence at the emission wavelength of the donor.

The present method of interrogation, when using read-out probes covering multiple target sequence repeats, is particularly useful in the analysis of long repeated sequence polymorphisms which do not require single-repeat resolution. An example is provided by Huntington's gene, which contains a polymorphic stretch of CAG tri-nucleotide repeats at the start of the protein-coding sequence. The disease is caused by an abnormally large expansion of this repeat in one copy of the gene. The present invention can be used to identify the repeat expansion in patient samples.

Figure 19A:
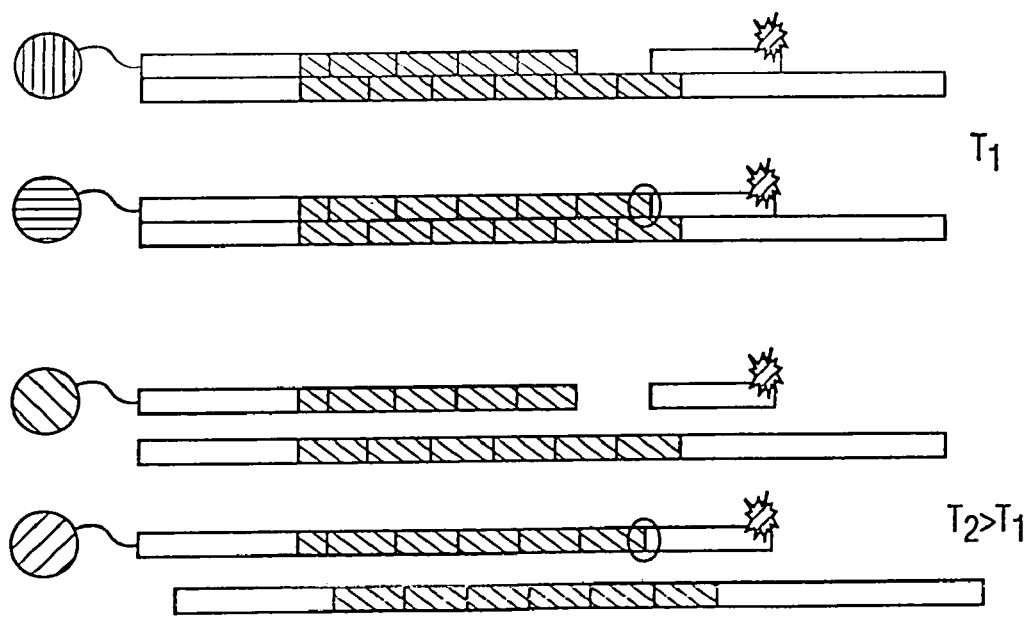
FIG. 19a is an illustration of identification of repeat sequence by ligation of interrogation probes ($T_1$ is the initial assay temperature and $T_2$ is the final assay temperature, wherein $T_2$ is greater than $T_1$).
Figure 19B:
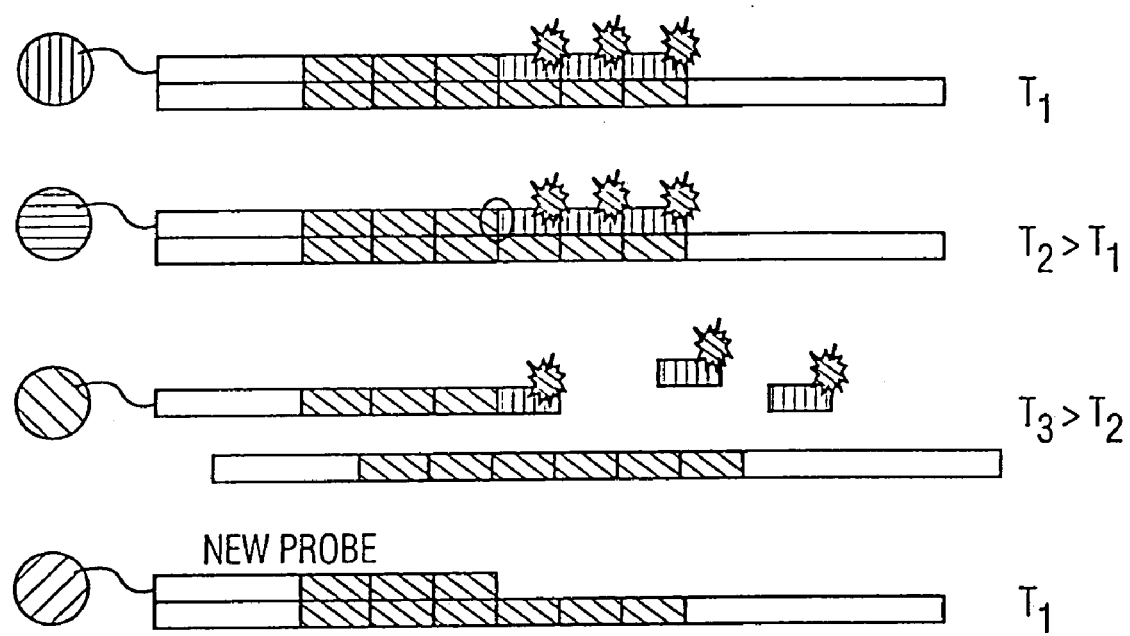
FIG. 19b is an illustration of the identification of repeat sequence by ligation and on-chip cycling ($T_1$, $T_2$ and $T_3$ indicate three assay different temperatures, wherein $T_3 > T_2 > T_1$).

Another embodiment involves the formation, at a first temperature, $T_1$, of a three-member hybridization complex with no gap between the interrogation probe and read-out probe, the latter of which is designed to contain, at or near its 3' terminus, a fluorescent dye. Subsequent to forming the three-member complex, the read-out probe is ligated to the interrogation probe at a second temperature, $T_2$, and the hybridization complex is denatured at a third temperature, $T_3 > T_m$ (where $T_m$ is the melting temperature), to leave a fluorescent strand indicating that the read-out probe terminated in the interior of the repeat section of the original hybridization complex. This method can be generalized to a dual-color detection format in which a second read-out probe with a different fluorescent dye anneals to the sequence in a region exterior the repeated sequence polymorphism (FIG. 19).

This method of interrogation permits linear on-chip amplification by repeatedly cycling between temperatures $T_1$, $T_2$ and $T_3$, each target sequence thereby serving as a template in the formation of a ligation product.

To the extent that the method for STR analysis, as disclosed in the present invention, is a general method for the analysis of repeated sequence elements and other polymorphisms in nucleic acids, it can be applied to the analysis of DNA from other than human origin.

For example, microbial DNA (such as bacterial DNA) can be analyzed to perform strain typing including the identification of drug resistant strains and to guide the selection of antibiotic treatments. DNA markers such as restriction length polymorphisms (RFLPs) and polymorphic tandem repeats (STRs, VNTRs) have been used for bacterial and yeast strain identification. This is particularly helpful when strains cannot be discriminated or distinguished by morphological and biochemical markers alone. A specific application is the strain typing of *Bacillus anthracis* (Anthrax) which is one of the most monomorphic bacterial species known. Five known strains have been identified on the basis of variable number of tandem repeats in the variable region of the vrrA gene.

Another application of the STR analysis method of the present invention is in the context of the identification and selection of specific genetic varieties displaying desirable traits. For example, these genetic markers are used to tag interesting traits determined by uncharacterized genetic factors with a closely linked well-defined polymorphic locus. Several classes of DNA markers that have been used for purposes of marker assisted selection (MAS), identification and plant variety protection, plant breeding, and fingerprinting include single site alterations (such as SNPs), as well as single and multi-locus repeat markers such as VNTRs, STRs, and simple sequence repeats (SSRs).

The present invention will be better understood from the following Examples. However, one skilled in the art will readily appreciate that the specific methods and results discussed herein are merely illustrative of the invention described in the claims which follow thereafter.

EXAMPLES

Example 1

Cystic Fibrosis Mutation Profile with Embedded Genetic Fingerprint

Figure 2:
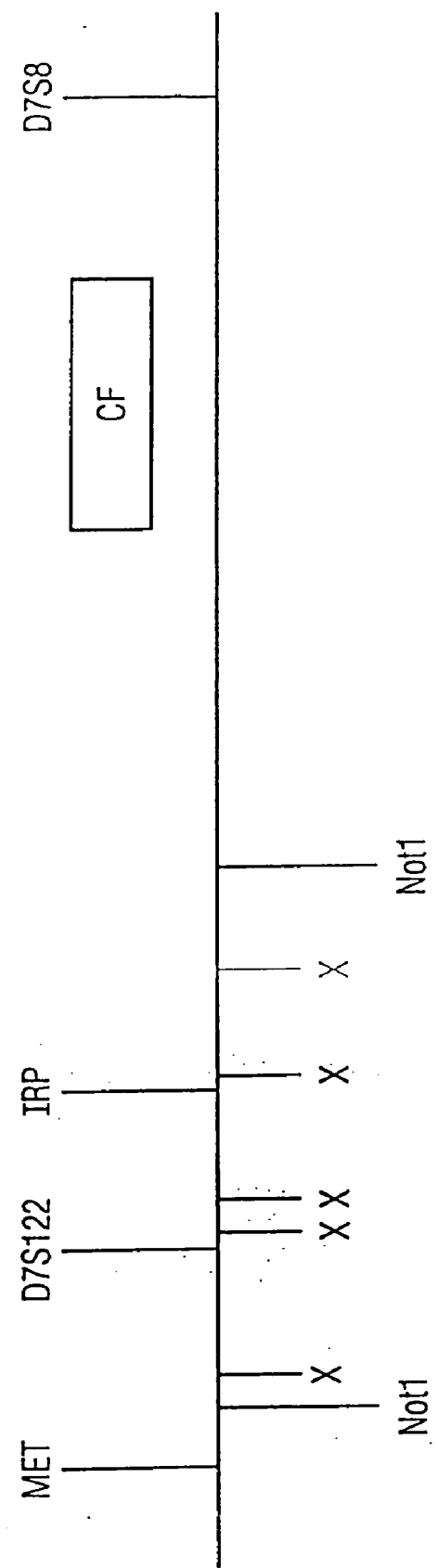
FIG. 2 is an illustration showing a restriction map for the CFTR region (X is an SNP marker, D7S122 and D7S8 are STRs, MET is methionine, NOT1 is restriction site and IRP is a gene).

In this Example, the analysis of mutations in the CFTR gene was performed so as to produce a genetic profile with an embedded panel of genetic identifiers as internal markers (FIG. 1). Most CF mutations of interest are located on exons 3 to 21 (FIG. 2 and Table 1). Given that the frequency of polymorphic markers within the CFTR gene does not differ significantly for CF patients as compared to the total population, the interrogation of these markers will not produce bias in the analysis of mutant versus normal chromosomes.

The choice of suitable primers ensures that sequence polymorphisms located within the CFTR gene are simultaneously amplified along with designated mutations to be probed by subsequent hybridization. In a preferred embodiment involving an array composed of encoded beads, one set of beads is modified with probes that are complementary to the CFTR mutations of interest and a second set of beads is modified with probes that are complementary to the selected intrinsic polymorphic ID markers. An aliquot of (amplified) patient sample is placed on the assembled bead array to generate and to record, in a single step, a genetic profile with embedded genetic ID. In a preferred embodiment involving random encoded bead array, the following are typical assay conditions.

Beads stained with different combinations of two fluorescent dyes were functionalized with neutravidin and biotinylated oligonucleotide probes, the latter step performed in TBS (10 mM Tris HCl, 0.5 M NaCl w/v) for 45 minutes at room temperature. The target was amplified using a forward primer 5'-labeled with Cy5 and a reverse primer modified with a phosphate group. Primer sequences were designed to be homologous either with intron sequences immediately flanking specific exons or with the sequences marking the beginning or end of certain exons. The use of such primers permits PCR amplification of the target gene concurrent with that of polymorphic markers located within the loci delineated by the chosen primers.

Figure 3:
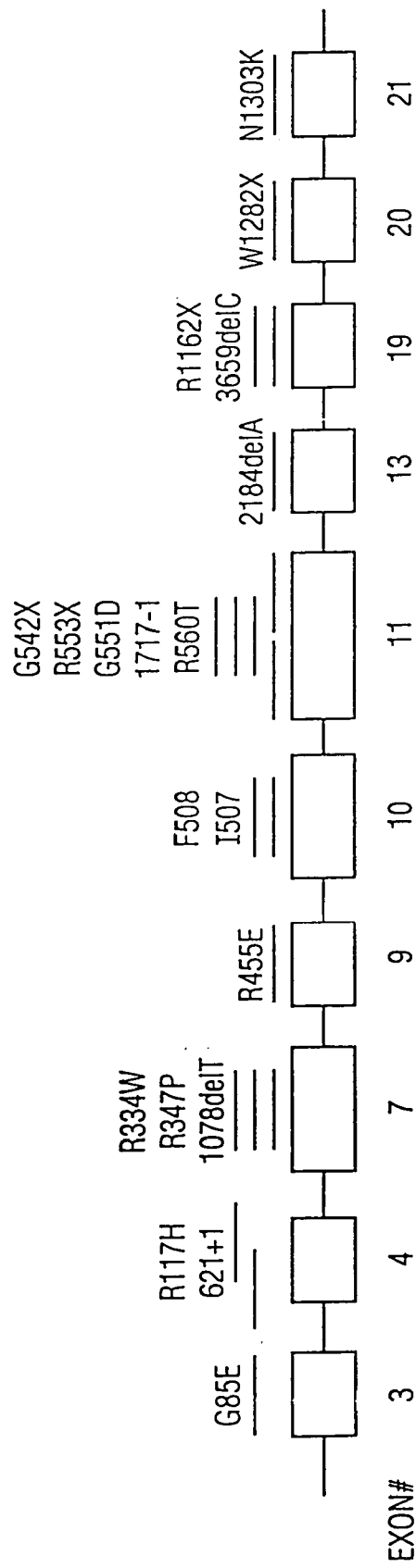
FIG. 3 is an illustration showing mutations within exons of the CFTR gene.

EXON 7 polymorphisms: When exon 7 containing three CF mutations (334W, 347P and 1078T), is amplified with a set of primers flanking its ends, sequence polymorphisms at positions dbSNP 100083 C/T, dbSNP 100084 C/G, dbSNP 100085 A/G, dbSNP 1799834 C/G, dbSNP 1800086 C/G, dbSNP 1800087 A/G are amplified as well (FIGS. 3 and 4). These polymorphisms represent intrinsic ID markers that are interrogated by hybridization to a corresponding set of oligonucleotide probes on encoded beads within a random array.

EXON 10 polymorphisms: The most common CF mutation, delta 508, is located on Exon 10. SNPs located on exon 10 including dbSNP 100089 C/T, dbSNP 100090 C/T, dbSNP 213950 A/G, dbSNP 100092 C/G, dbSNP 1801178 A/G dbSNP 180093 G/T, dbSNP 180094 A/G and dbSNP 1900095 G/T (FIG. 5) can be amplified along with the mutation and interrogated by hybridization to a corresponding set of oligonucleotides on encoded beads within random array.

Genomic DNA extracted from patient samples was amplified using a set of primers in a multiplex PCR (mPCR) reaction. A preferred embodiment of a mPCR protocol for cystic fibrosis analysis (L. McCurdy, Thesis, Mount Sinai School of Medicine, 2000, which is hereby incorporated by reference) is as follows. Multiplex PCR was performed using chimeric primers tagged, at their respective 5' ends, with a universal sequence to narrow the range of respective melting temperatures. PCR primers were synthesized to contain a Cy5 or Cy55 (Amersham) label on the 5' end. Using a Perkin Elmer 9600 thermal cycler, 28 cycles of amplification were performed, each cycle consisting of a 10 second denaturation step at 94° C. with a 48 second ramp, a 10 second annealing step at 60° C. with a 36 second ramp and a 40 second extension step at 72° C. with a 38 second ramp. Each reaction mixture of 50 µl contained 500 ng of genomic DNA, 1× PCR buffer (10 mM Tris HCl, 50 mM KCl, 0.1% Triton X-100), 1.5 mM MgCl2, 200 uM each of PCR grade dNTPs and 5 units Taq DNA polymerase. Optimal primer concentrations were determined for each primer pair.

Figure 6:
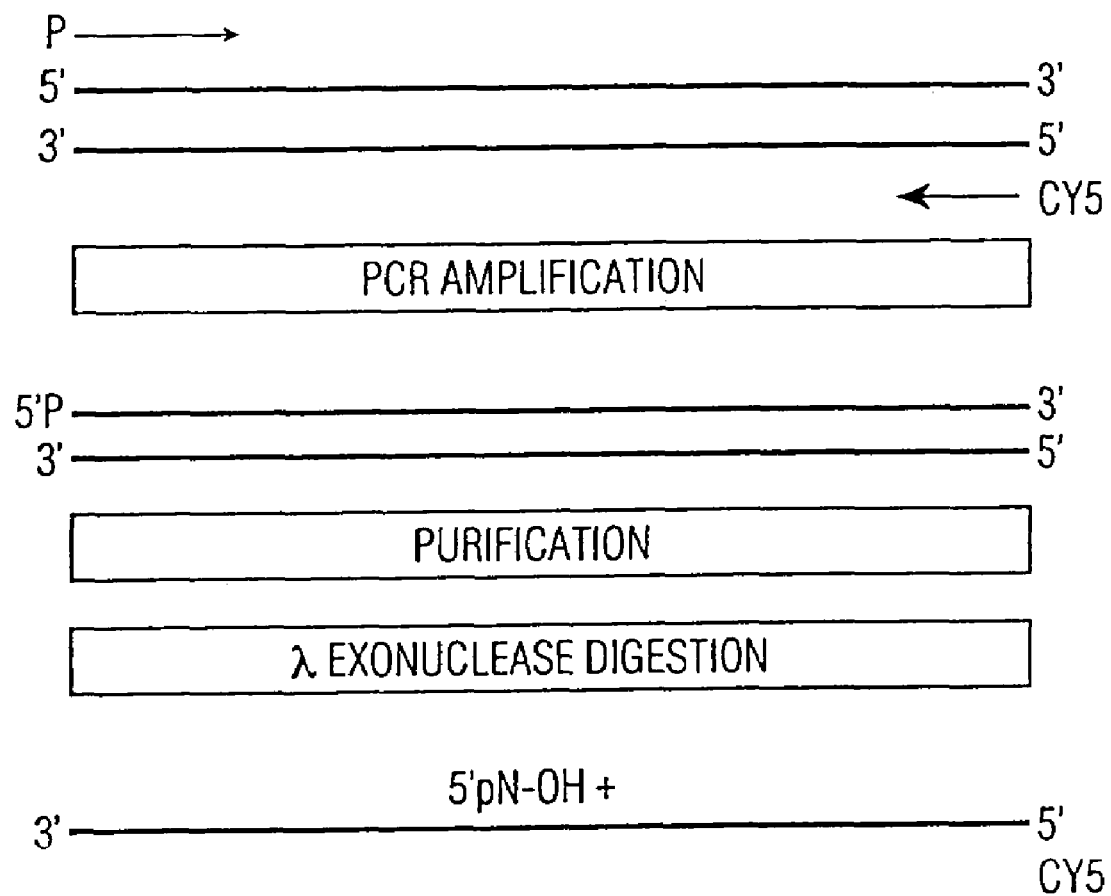
FIG. 6 is an illustration showing a protocol for PCR analysis with phosphorylated primers.

Following amplification, products were purified to remove all reagents and the DNA concentration was determined by spectrophotometric analysis. To generate a single-stranded target, PCR products (200 ng) were incubated with 2.5 units of (lambda) exonuclease in 1× buffer at 37° C. for 20 min and inactivated at 75° C. for 10 min. Under these conditions, the enzyme digests one strand of duplex DNA from the 5'-phosphorylated end and releases 5' phosphomononucleotides (FIG. 6). The products were used directly in a hybridization mixture (2.25 M TMAC, 0.15% SDS, 3 mM EDTA).

For each hybridization reaction, 5 µl of hybridization mixture were placed on the surface of silicon chips, each chip carrying an array of encoded beads displaying oligonucleotide probes. Chips were placed in a covered dish and placed on a shaking surface (~200 rpm) in an incubator at 55° C. for 15 minutes. Chips were washed by flushing the array three times with 1× TMAC buffer. The Cy5 fluorescence signal from each bead within the array was recorded and analyzed using a fluorescence microscope, CCD camera and image analysis software to determine the mutation profile.

Example 2

Duchenne Muscular Dystrophy Mutation Profile with Embedded Genetic Fingerprint

This Example illustrates the design of a genetic ID for Duchenne muscular dystrophy (DMD), an X-linked recessive trait mostly occurring in males that is characterized by progressive loss of muscle strength. Although DMD protein (dystrophin) analysis of muscle provides an accurate diagnostic test, it is invasive and carries high cost and risk. Further, because the protein is not expressed in amniotic fluid or in chorionic villus tissue, the protein test is not suitable for prenatal diagnosis. On the other hand, the DMD gene has been cloned and several deletions have been identified (FIG. 7), with Southern blots requiring hybridization with ten cDNA probes. (Kunkel, et al, Nature, 322:73-77 (1986)).

Figure 7:
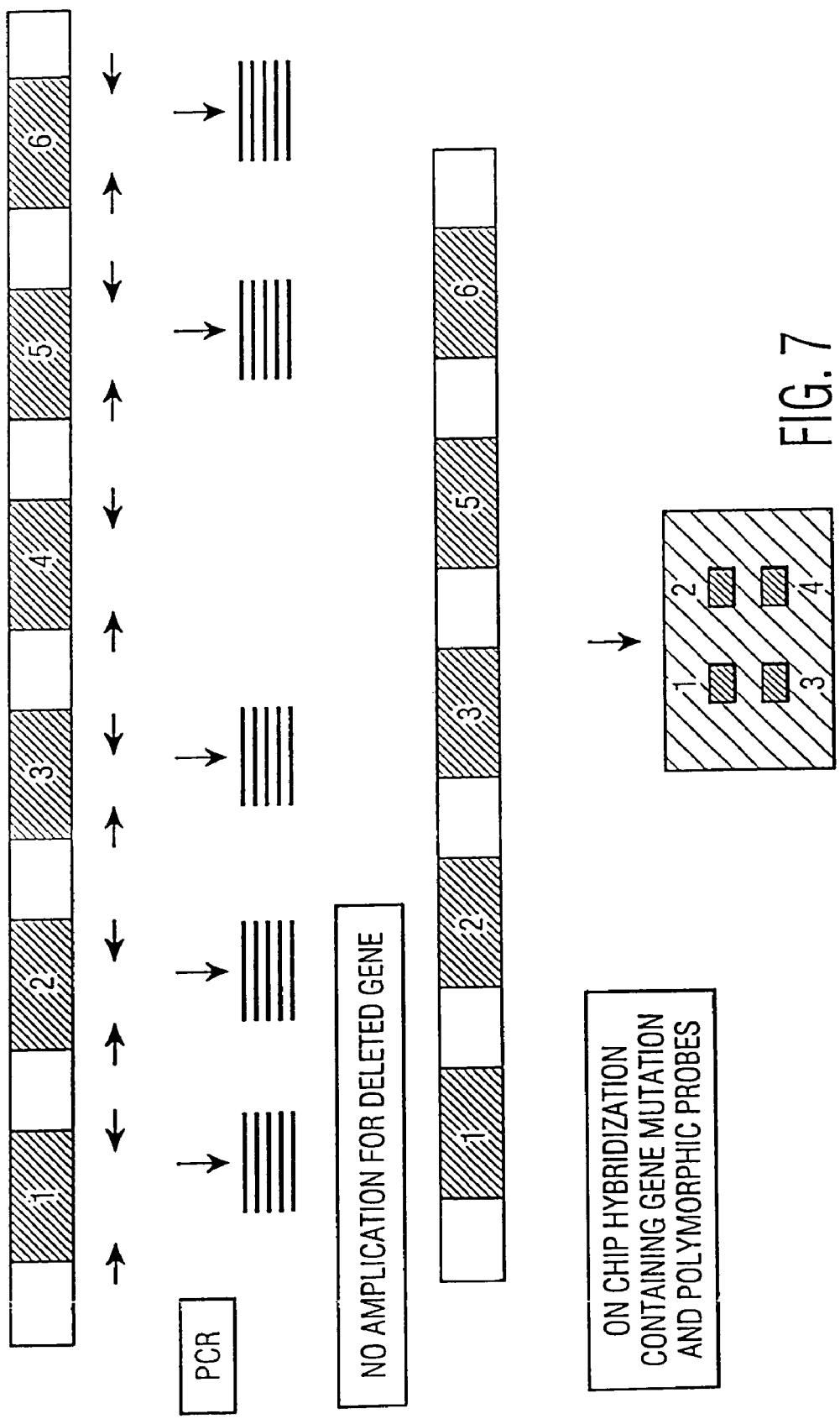
FIG. 7 is an illustration showing a protocol of analyzing dystrophin gene deletions. Most polymorphic markers are deletions in this gene. Primers can be designed to amplify flanking sequence of exons where deletions occur. The deleted sequences and polymorphic markers can be identified simultaneously.

A multiplex PCR protocol has been described for the simultaneous analysis of these gene deletions. (Monaco et al, Nature, 323:646-650 (1986)). An intrinsic genetic ID can be derived from a set of several dinucleotide repeat polymorphisms located at many sites within the DMD gene. FIG. 7 illustrates a protocol for the analysis of gene deletions and polymorphic ID markers within the DMD gene. PCR primers are designed to flank exon sequences such that the presence of a deletion within the flanked sequence blocks target amplification, leading to a null result in subsequent interrogation.

Example 3

Matching Genetic Profiles to Genetic Fingerprint Records

Given a genetic fingerprint recorded by known methods of DNA fingerprinting, such as, for example, the methods used as part of neonatal testing or those applied to entire selected populations (e.g., members of the defense forces or prison inmates), the methods of the present invention provide a means for authenticating the genetic fingerprint concurrently with genetic testing. For example, markers, such as STRs, that are recorded for paternity and forensic analysis could be used. In addition, markers derived from SNP genotyping or haplotyping could be used. Consequently, a genetic profile with embedded genetic ID would be unambiguously linked to a specific patient record by way of matching genetic IDs. For example, a person's genetic fingerprint may be recorded in a database along with other genetic data according to the methods of this invention. If an individual is then subjected to a subsequent genetic test (for example, for any genetic disease or haplotyping), the results of the second test may be verified unambiguously by comparing the genetic fingerprints associated with the first and second tests.

Example 4

On-chip Identification of STR Length Polymorphism in TH01

The HUMTH01 locus contains tetranucleotide repeats (CATT) in the Tyrosine Hydroxylasegene. To determine the length of these STR polymorphisms, oligonucleotides probes were synthesized to contain a 5' anchor sequence of six-nucleotides designed to be complementary to the target's trailing sequence as well as a 3' anchor sequence of six nucleotides designed to be complementary to the target's leading sequence, as follows:

```
5' ttc cct - - - cac cat 3'
```

To determine the length of the repeated sequence in the target, a set of oligonucleotides probes is provided to contain one probe matching in length, and thus matching in the number of repeated CATT sequence elements, any anticipated number of complementary target repeats. In this design, only the probe containing the correct number of tetramer repeats will form a hybridization complex with the target in which both 5' anchor and 3' anchor are properly aligned with the target's trailing and leading sequence, respectively, and only correctly aligned probes are extended to produce a positive assay signal.

Figure 9A:
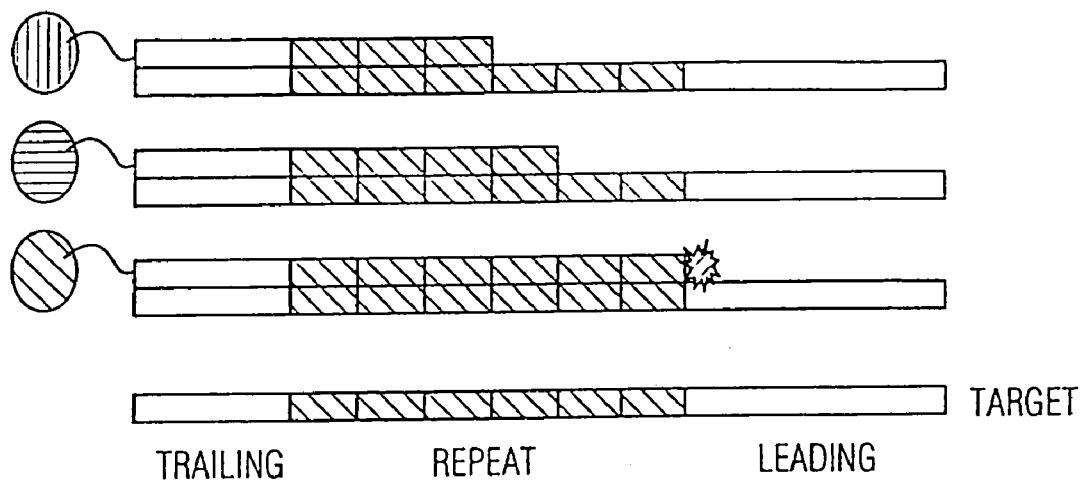
FIG. 9a is an illustration of probe design for STR length polymorphism with an anchor sequence using labeled ddNTPs.
Figure 9B:
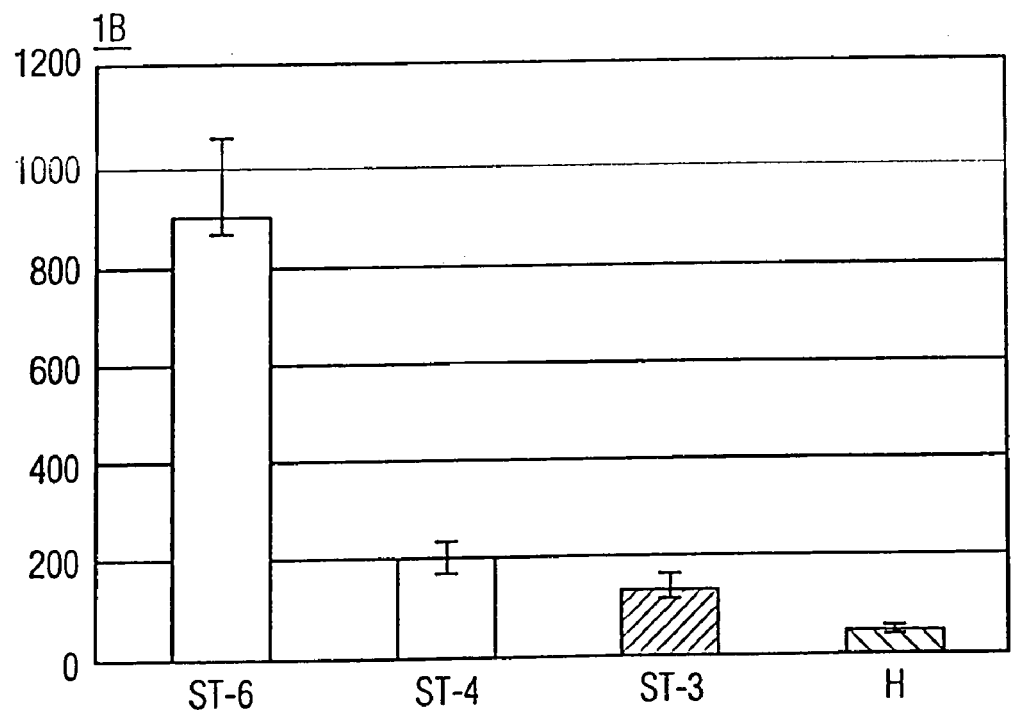
FIG. 9b is an illustration of results with the THO1 locus using an STR polymorphism.

Oligonucleotide probes were synthesized to contain 17 nucleotides and a biotin label attached to the 5' end by way of a 12-C spacer (Biotin-TEG) (FIG. 9a) and were purified using reverse phase HPLC by a commercial vendor (Synthegen TX). Using the biotin moiety, probes were attached to streptavidin-coated encoded beads which were assembled into a planar array on a silicon chip. One micromole of a single-stranded target containing six CATT repeats in a hybridization mixture containing 10 mM Tris-HCl (pH 7.4) 1 mM EDTA, 0.2 M NaCl and 0.1% Triton X-100 was placed in contact with the random encoded bead array and incubated at 50° C. for 20 minutes. The hybridization mixture was then replaced by a mixture containing 3 U of Thermo Sequenase (Amersham Pharmacia Biotech NJ), and 1× enzyme buffer with TAMRA-labeled dideoxynucleotide (ddNTP) analogs (NEN Life Sciences) and probe extension was allowed to proceed for 3 minutes at 60° C. The annealing and elongation reactions can be performed in a single step by adding ddNTPs or dNTPs in the mixture and running the reaction at two temperatures. The bead array was then washed with distilled $H_2O$ for 15 minutes and an image containing the fluorescence signal from each bead within the array was recorded using a fluorescence microscope and a CCD camera. Images were analyzed to determine the identity of each of the extended (and hence fluorescent) probes. As shown in FIG. 9b, the largest signal was recorded from beads displaying the six-tetramer probe ST-6, indicating that this probe contains the correct number of repeats to match the number of target repeats.

Example 5

Figure 10A:
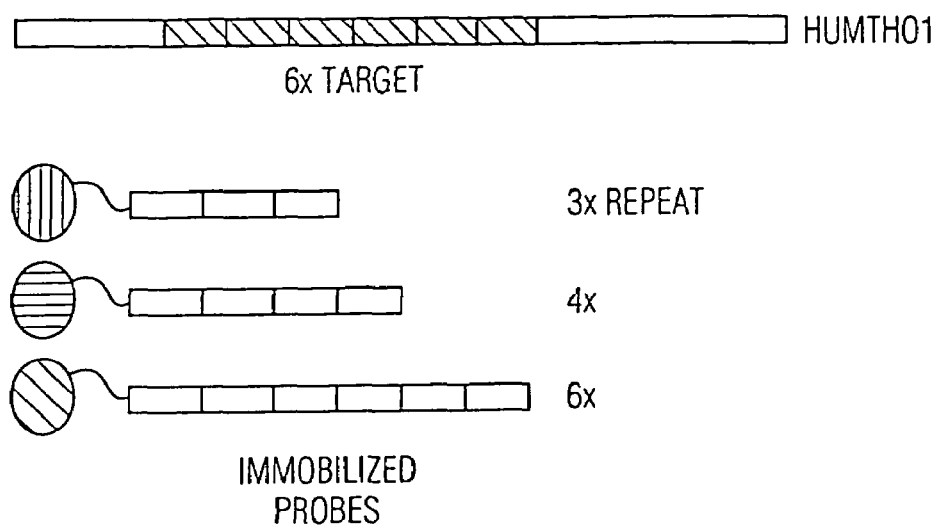
FIG. 10a is an illustration of probe design for an STR length polymorphism without an anchor sequence.

On Chip Identification of STR Length Polymorphism Using Probes Containing a 3' Anchor ("Hook") Sequence Oligonucleotides designed to contain a short 3' anchor ("hook") sequence (but not a 5' anchor sequence) were attached to encoded beads (FIG. 10a). Specifically, probes respectively containing 3, 4, and 6 tetramer repeats were designed to interrogate a target fragment containing six tetramer repeats flanked by 5' leading sequence and a 3' trailing sequence.

In this design, all probes will form a hybridization complex with the target in which the probe's 3' anchor sequence is properly aligned with the target's leading sequence. However, by setting the assay temperature at a value exceeding the melting temperatures of all but the longest probe, only hybridization complexes containing that probe remain, and only that probe is extended to produce a positive assay signal.

Figure 10B:
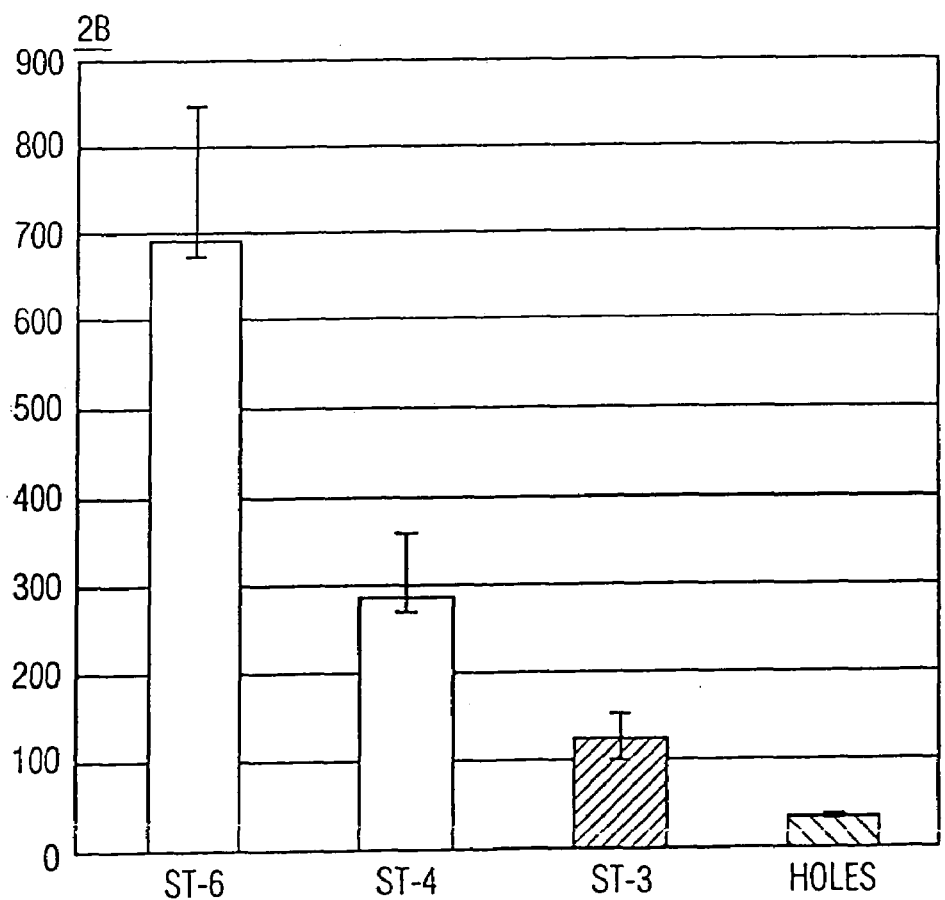
FIG. 10b is an illustration of results with THO1 locus using probes without an anchor.

Single base extension was performed in the presence of DNA polymerase and ddGTP as previously described herein As expected, the largest signal was recorded from beads displaying the six-tetramer probe (FIG. 10b). These results demonstrate the high level of discrimination produced by the compositions and methods of the present invention.

Example 6

Figure 11A:
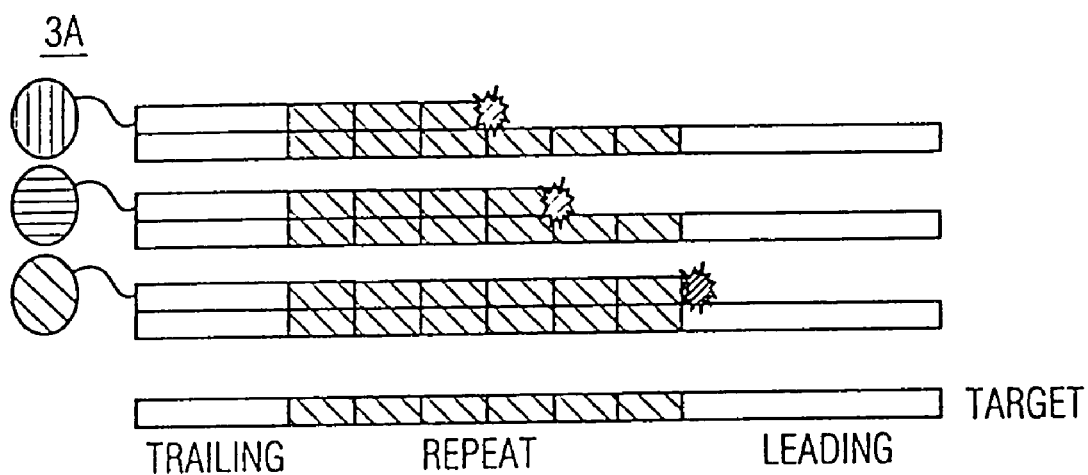
FIG. 11a is an illustration of on-chip STR length polymorphisms with two differentially labeled ddNTPs. In this case, the ddNTPs are differentially labeled with different colors.
Figure 11B:
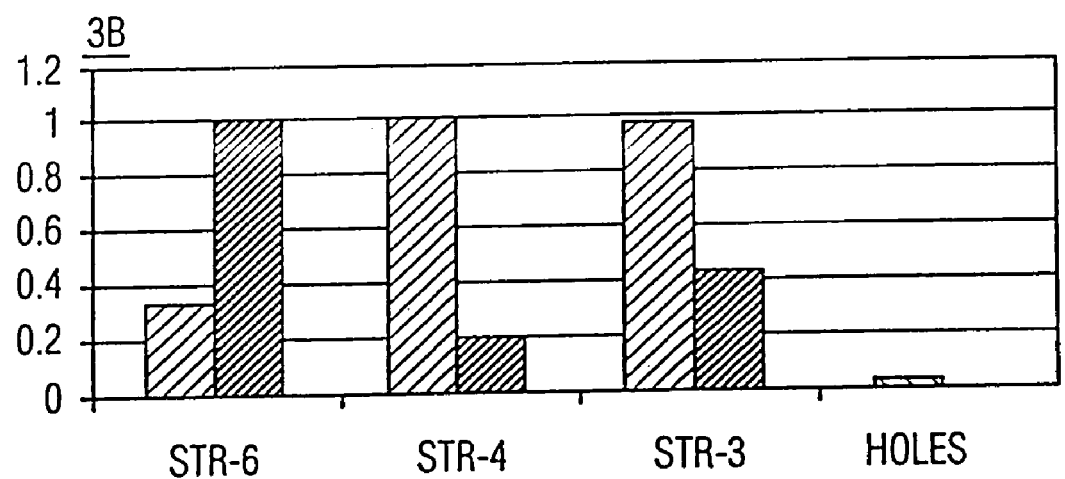
FIG. 11b is an illustration of the results obtained with two differentially labeled ddNTPs where the green-colored ddNTP is incorporated with the correct match and the orange colored ddNTP is incorporated when the probe terminates within the repeat.

On-chip Identification of STR Length Polymorphism Using Dual Color Detection Oligonucleotides were designed as in Example 4, but the single base extension reaction was performed in the presence of two ddNTPs respectively labeled with TAMRA (green) and fluorescein (orange) (NEN Life Sciences) (FIG. 11a). The green ddNTP is incorporated if the annealed probe terminates exterior to the repeated sequence (external marker) while the orange ddNTP is incorporated if the annealed probe terminates interior to the repeated sequence (internal marker). A target containing six tetramer repeats was added to the solution, and the assay and integrated analysis were performed as described earlier. As before, high signal recorded in the green channel produced by extension of the six tetramer probe ST-6 indicated that this probe contained the correct number of repeats. In addition, however, high signal in the orange channel produced by extension of the three-tetramer probe ST3 and the four-tetraner probe ST4 indicated that these probes terminated interior to the repeated sequence and contained an incorrect number of repeats (FIG. 11b). This dual color format affords additional confirmation of assay results by producing a positive signal for all probes in the set.

Example 7

Effect of Anchor Length on Probe Slippage

Two sets of oligonucleotide probes were synthesized to contain, in addition to three, four and six tetramer repeats, 5' anchor sequences of respectively six and eleven nucleotides for the two probe sets, as well as identical 3' anchor sequences, as follows:

```
5' ttc cct - - - cac cat 3'

5' ctt att tcc ct - - - cac cat 3'
```

As before, the 5'-anchor sequence was designed to be complementary to the target's trailing sequence flanking the repeats. To determine the length of the repeated sequence in the target, a set of oligonucleotides probes was provided to contain one probe matching in length, and thus matching in the number of repeated CATT sequence elements, any anticipated number of complementary target repeats.

Figure 12:
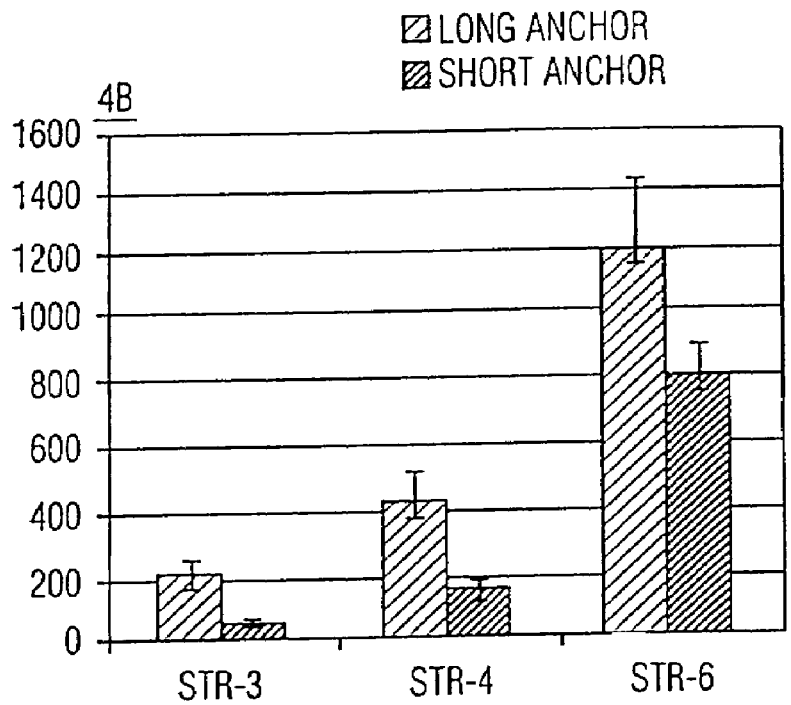
FIG. 12 is an illustration of the effect of anchor length on SBE for STR polymorphism analysis using two anchors of six or eleven bases.

Using reaction conditions as described earlier (Example 4), probes containing the longer 5' anchor sequence produced a higher signal level than did probes containing the shorter 5' anchor sequence, indicating higher stability of the hybridization complexes formed by the longer probes. (FIG. 12). The anchor sequence can be varied to fit the experimental requirements.

Example 8

Effect of Annealing Temperature on the Specificity of STR Polymorphism Analysis

Figure 14:
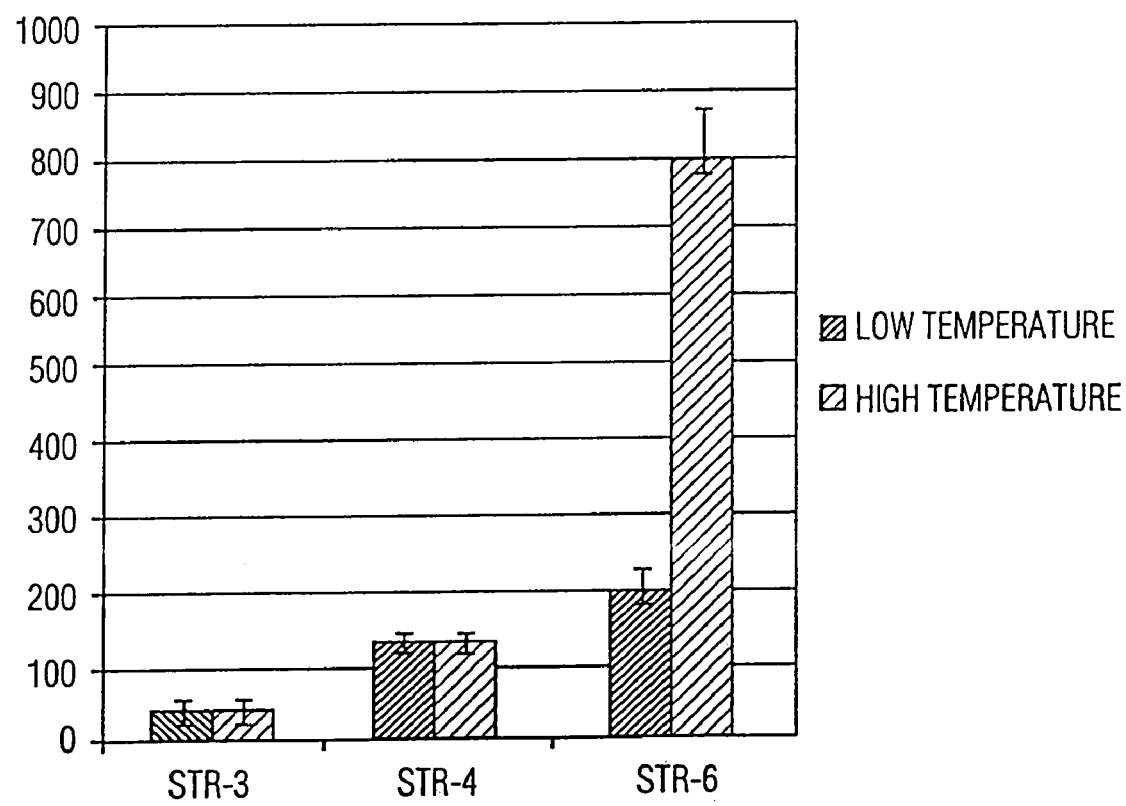
FIG. 14 is an illustration of the effect of annealing temperature on SBE for STR polymorphism analysis.

Oligonucleotide probes were designed, and single base extension was performed as in Example 5, but at two different annealing temperatures, namely at 37° C. and at 50° C. The image analysis of results obtained at 50° C. showed high discrimination between the ST-6 probe containing the correct number of repeats and the other probes containing an incorrect number of repeats, while image analysis of results obtained at 37° C. showed essentially no discrimination (FIG. 14). Selection of the correct assay temperature substantially enhanced the specificity of detection.

Example 9

Sense and Anti-sense Probes

This Example illustrates the use of oligonucleotides probes containing neither 5'- nor 3'-anchor sequences for the analysis of both sense and anti-sense DNA strands. Oligonucleotide probes containing such anchor sequences complementary to trailing and leading sequences in both sense and anti-sense DNA also can be used in other embodiments. Both sets of probes are attached to encoded beads which are separately assembled on the surface of two silicon chips that are placed on the same chip carrier. The target is amplified with two sets of primers, each target containing six repeats as well as a 3' trailing sequence and a 5' leading sequence. Single base extension is performed in the presence of DNA polymerase and ddNTPs as described in Example 5. In this design, extension occurs only for the probe containing the correct number of repeats to match the number of target repeats.

Example 10

Poly T Identification

Figure 16:
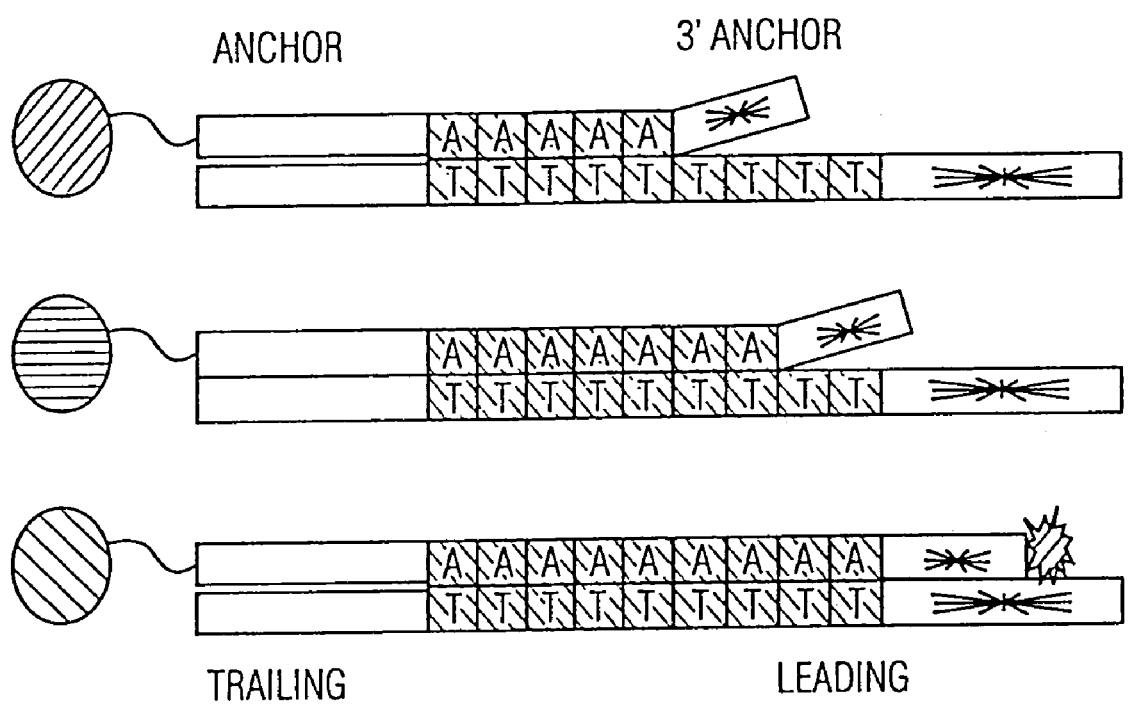
FIG. 16 is an illustration of probe sequence design for the identification of poly-T variants in intron 8 of the CFTR gene.

Oligonucleotide probes were designed for the identification of intron 8 poly-thymidine (T) tract variants (5T, 7T, 9T) within the CFTR gene. Each probe was synthesized and purified using reverse phase HPLC by a commercial vendor (IDT) to contain a biotin label attached to the 5' end by way of a 12-C spacer (Biotin-TEG). Probes were designed to contain both a 5' anchor sequence matching the 3' trailing sequence of the target and a 3' anchor ("hook") sequence matching the 5' leading sequence of the target. The anchor sequence length was varied between four and ten bases; longer anchor sequence lengths also are possible (FIG. 16). Probes containing variable numbers of repeats were immobilized on encoded beads as described earlier.

In this design, only the probe that aligns with the target sequence and matches the number of target repeats will be elongated in the presence of DNA polymerase. In the elongation step, dNTPs are provided, either at least one fluorescently labeled dNTP to produce a fluorescently labeled elongation product, or one or more labeled ddNTPs for single base extension as described in previous examples. The signal is recorded by instant imaging of the array as described in this application. The results of experiments using targets containing poly-T variants of different lengths demonstrate that identification of respective poly-T variants is achieved.

Example 11

Identification of Poly T Variant of CFTR Gene

The melting temperature, $T_m^{(n)}$ of a given hybridization complex containing an nT variant reflects the length of the variant as well as the degree of mismatch between probe and target. That is, discrimination is optimized by setting the assay temperature so as to destabilize all hybridization complexes except those containing probes either matching or exceeding the length of the poly-T sequence in the target. For example, a target containing a 7T variant is readily identified by setting the assay temperature T, so as to satisfy the condition $T_m^{(5)} < T < T_m^{(7)}, T_m^{(9)}$.

To perform the assay, 1 μmole of target was added to an annealing and elongation mixture containing 10 mM Tris-HCl (pH 7.4) 1 mM EDTA, 0.2 M NaCl, 0.1% Triton X-100, 3 U of Thermo Sequenase (Amersham Pharmacia Biotech NJ), along with TAMRA-labeled dideoxynucleotide (ddNTP) analogs (NEN Life Sciences).

Figure 17A:
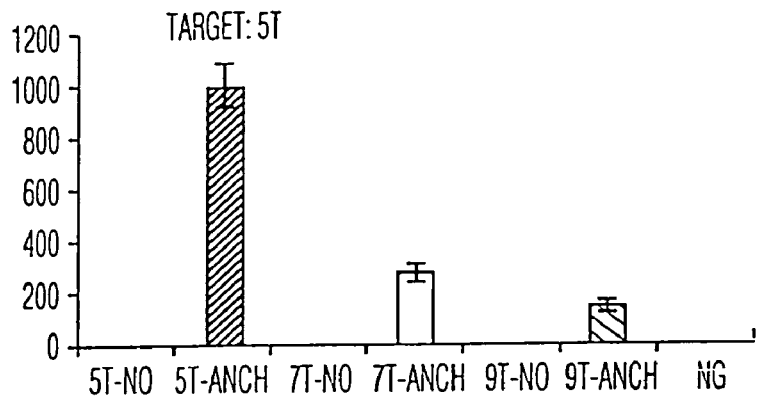
FIG. 17 is an illustration of the results of identification of various targets using poly-T variants in intron 8 of the CFTR gene.
Figure 17B:
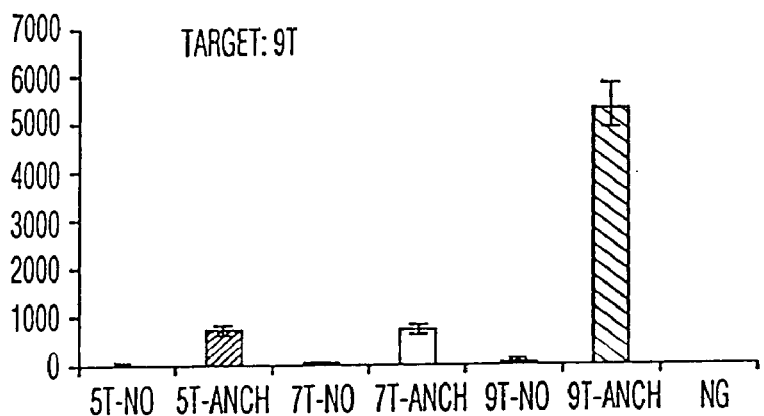
Figure 17C:
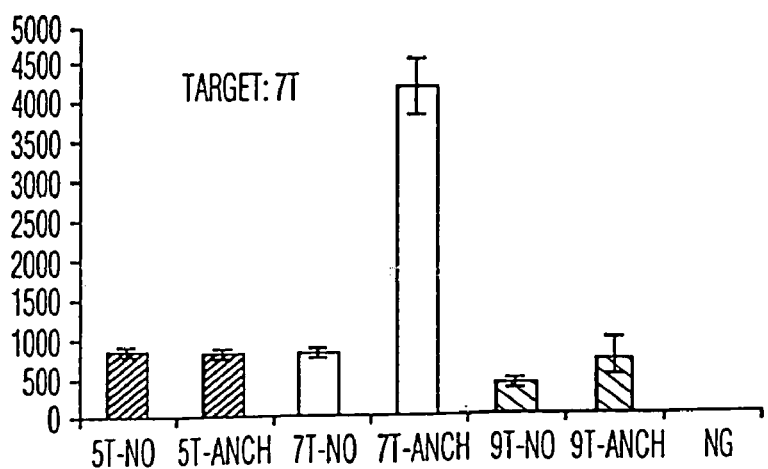

Following annealing and elongation, bead arrays were washed with distilled $H_2O$ for 15 minutes. An image containing the fluorescence signal from each bead within the array was recorded using a fluorescence microscope and a CCD camera, and images were analyzed to determine the identity of each of the elongated primers. The results in FIG. 17 demonstrate that polyT variants in the target are properly identified by the compositions and methods of the present invention.

Example 12

Hierarchical Probe Design for the Analysis of Long Repeats

Figure 18:
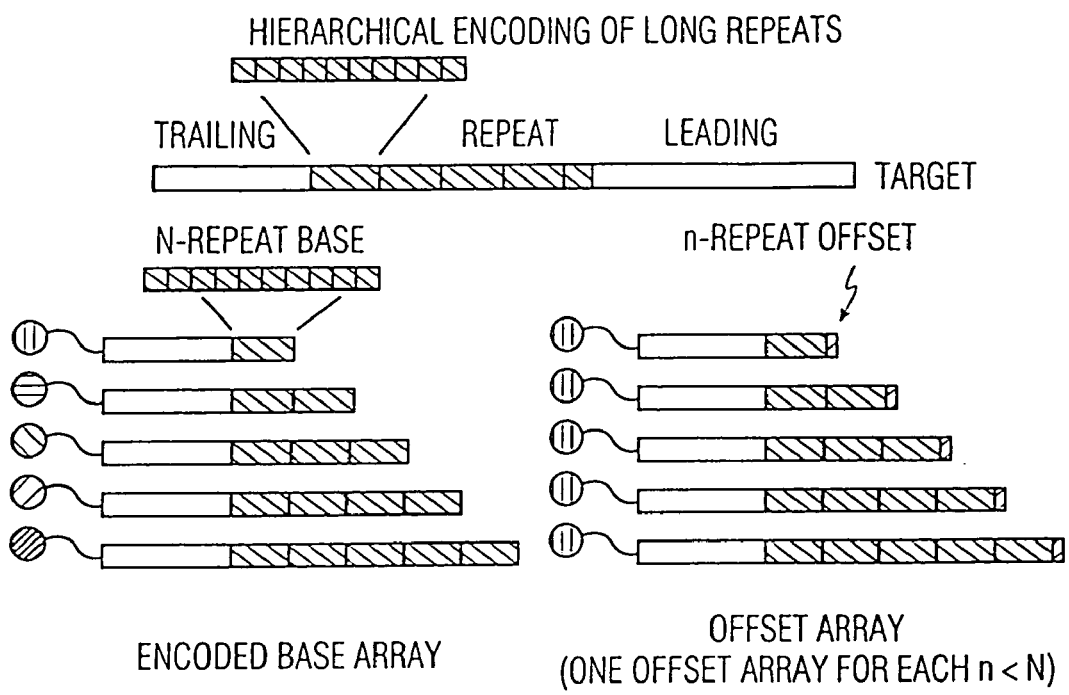
FIG. 18 is an illustration of the probe sequence design for the identification of longer repeats, such as those that are ten (10) to several hundreds of bases long.

This example illustrates an approach to the design of probes for the analysis of long target repeats that are common in many genetic diseases. This approach involves a "base-offset" construction wherein a first set of "base" probes is constructed to contain 1N, 2N, 3N, . . . (N>1) repeats, with these "base" probes being attached to separate encoded beads. A second set of "offset-probes" is constructed to contain all N+n repeats, with n<N. Importantly, to minimize the number of codes required, all probes containing the same offset are attached to the same type of encoded bead. FIG. 18 depicts two separate probe designs with common factors such as 5' anchor sequence.

This approach is particularly useful when single-repeat resolution is not required for diagnosis. For example, in the diagnosis of predisposition to certain disease states (such as Huntington's disease), it is critical to determine with single repeat resolution only the number of repeats between 35 and 41, the critical range determining the likelihood of pathology. That is, patients with more than 41 repeats will develop the disease while patients with fewer than 35 repeats will not, with the probability of pathology increasing with repeat number between 35 and 41.

For example, to determine the number of target repeats up to 42 to within a resolution of seven, (i.e., N=7), six "base-probes" are constructed to respectively contain 7, 14, 21, . . . , 42 repeats. These probes are attached to encoded beads. Under assay conditions described in previous examples, all but those hybridization complexes containing probes with a number of repeats matching or exceeding the number of target repeats will be destabilized. For example, by setting the assay temperature, T, to an appropriately high value to exceed $T_m^{(35\ repeats)}$, a number that is readily determined with great precision prior to the assay, a sample containing 32 target repeats produces a signal only for the base probes containing 35 and 42 repeats while a sample containing 39 target repeats produces a signal only for the base probes containing 42 repeats. In the first case, no further analysis is required. In the second case, the target is determined to contain at least 35 repeats, and a set of "offset probes" is invoked to determine the exact number. Here, offsets, n<7, vary between 1 and 6, and probes sharing the same offset number are grouped. That is, those probes with 0+1, 7+1, 14+1, . . . 35+1 repeats, those with 0+2, 7+2, 14+2, . . . 35+2 repeats, and so on up to those with 0+6, 7+6, 14+6, . . . 35+6 repeats are grouped ("pooled") and attached to the same type of encoded bead. Under assay conditions described above, the sample containing 39 repeats produces a signal for offset probes n=4, 5 and 6 but not for offset probes n=1, 2 and 3 because the former three groups respectively contain probes with 35+4, 35+5 and 35+6 repeats while the largest number of repeats represented in the latter three groups, 35+3, does not match or exceed the number of target repeats. This set of assay readings determines the exact number of target repeats.

A related design invokes two sets of "base probes", the second set shifted with respect to the first. In the example described above, a second set of base probes shifted by ΔN=3 would contain probes with 0+3, 7+3, 14+3, . . . 35+3 repeats, each attached to encoded beads. For the patient sample with 39 repeats, the first set of base-probes produced a signal only for the base probe with 42 repeats thereby placing the number of target repeats to >35; the second set of base-probes produces no signal at all, placing the number of target repeats to >38. This alternative design using multiple shifted sets of offset probes is particularly useful to bracket the number of target repeats.

Example 13

Identification of Polymorphic Repeats by Ligation and on Chip Cycling

In this Example, an experiment designed to identify the number of repeats in the TH01 locus uses ligation to attach a labeled detection probe to an adjacent immobilized capture probe within a three-member hybridization complex formed by the two probes and the target.

The detection probes are designed to be complementary to the leading sequence of the target (as in Example 1) and to a portion of the repeat sequence. At a first temperature, $T_1$, the target will anneal to an immobilized capture probes A detection probe is added, at either the first, or preferably at a second, higher temperature, $T_2 > T_1$, and is permitted to anneal to the leading sequence of the target but is ligated only if it contains the correct number of target repeats. At a third temperature, $T_3 > T_1$, $T_2$, chosen so as to destabilize non-ligated three-member hybridization complexes, signal remains only on those beads retaining ligated detection probe (FIG. 19a). These beads identify the probes with the correct number of repeats.

In a variation of the above design, the assay is cycled multiple times through the sequence $T_1 < T_2 < T_3$ to permit each individual target strand to mediate multiple ligation reactions. Under conditions ensuring an excess of capture and detection probes, cycling results in linear signal amplification. This assay can be performed in a portable thermocycler with instant imaging at every temperature.

We claim:

1. A method of sequence-specific amplification of assay signals produced in the analysis of a target nucleic acid sequence, the method permitting real-time monitoring of amplified signal and comprising the following steps:

(a) providing a temperature-controlled sample containment device that permits real-time recording of optical assay signals produced within said device, and a temperature control means for controlling the temperature of said device;

(b) providing within said sample containment device a set of interrogation probes, said interrogation probes being capable of forming a hybridization complex with a target nucleic acid and being attached to beads, wherein said beads are associated with a chemically or physically distinguishable characteristic that identifies the interrogation probes attached thereto;

(c) contacting said interrogation probes with the target sequence to form a hybridization complex between the interrogation probes and the target sequence;

(d) contacting said hybridization complex with a second oligonucleotide probe, said second probe comprising a label and capable of being ligated to the interrogation probes contained within the hybridization complex;

(e) providing conditions suitable for ligating said second labeled oligonucleotide probe to the interrogation probe;

(f) detecting the optical signals from the second labeled probes; and (g) performing one or more annealing-ligating-detecting-denaturing cycles, each cycle increasing the number of ligated probes in arithmetic progression and involving the following steps:

(i) providing a first temperature for the formation of the hybridization complex;

(ii) providing a second temperature for ligase-catalyzed ligation of the interrogation probe and the second labeled probe to occur to thereby generate a ligation product, wherein ligation is associated with a change in optical signature of beads associated with the ligation product;

(iii) imaging and/or recording optical signals from the ligation product thereby permitting real-time monitoring of amplified signal emanating from the ligation product; and (iv) providing a third temperature for denaturing all hybridization complexes.

2. The method of claim 1 wherein steps (c) to (g) are repeated one or more times.

3. The composition of claim 1 wherein the target nucleic acid sequences are derived from the patient genomic sample by amplification of one or more nucleic acid subsequences within the patient genomic sample.

4. The composition of claim 3 wherein the amplification is performed using the polymerase chain reaction.

5. The method of claim 1, wherein the target nucleic acid sequence includes a mutation site or a polymorphic site and said set interrogation probes includes members designed to detect the different nucleotides at the mutation or polymorphic site.

6. The method of claim 1, wherein the target sequence includes a mutation site or a polymorphic site and the set of interrogation probes includes members capable of annealing to subsequences in the target sequence including the mutation site or the polymorphic site, within a range of proximity to the mutation site or the polymorphic site.

7. The method of claims 5 or 6, wherein the polymorphic site is a single nucleotide polymorphism.

8. The method of claims 5 or 6, wherein the polymorphic site is a short term tandem repeat site.

9. The method of claim 1 wherein the label is an inorganic nanoparticle label, including semiconductor Quantum Dot particles and Resonant Light Scattering metal nanoparticles.

* * * * *